US009947505B2

(12) United States Patent
Russo et al.

(10) Patent No.: US 9,947,505 B2
(45) Date of Patent: Apr. 17, 2018

(54) GRAPHENE MODIFICATION

(71) Applicant: MEDICAL RESEARCH COUNCIL, Swindon (GB)

(72) Inventors: Christopher J. Russo, Cambridge (GB); Lori A. Passmore, Cambridge (GB)

(73) Assignee: MEDICAL RESEARCH COUNCIL, Swindon (GB)

( * ) Notice: Subject to any disclaimer, the term of this patent is extended or adjusted under 35 U.S.C. 154(b) by 0 days.

(21) Appl. No.: 14/911,718

(22) PCT Filed: Aug. 7, 2014

(86) PCT No.: PCT/GB2014/052423
§ 371 (c)(1),
(2) Date: Feb. 11, 2016

(87) PCT Pub. No.: WO2015/022500
PCT Pub. Date: Feb. 19, 2015

(65) Prior Publication Data
US 2016/0203942 A1 Jul. 14, 2016

Related U.S. Application Data

(60) Provisional application No. 61/865,359, filed on Aug. 13, 2013.

(30) Foreign Application Priority Data

Oct. 18, 2013 (GB) .................................. 1318463.5

(51) Int. Cl.
*H01J 37/20* (2006.01)
*B08B 7/00* (2006.01)
(Continued)

(52) U.S. Cl.
CPC ............ *H01J 37/20* (2013.01); *B08B 7/0035* (2013.01); *C01B 32/182* (2017.08);
(Continued)

(58) Field of Classification Search
CPC .... H01J 37/20; H01J 37/26; H01J 2237/2007; H01J 2237/2602; B08B 7/0035;
(Continued)

(56) References Cited

U.S. PATENT DOCUMENTS

2009/0291270 A1* 11/2009 Zettl ..................... B81C 99/008
428/195.1
2012/0194813 A1 8/2012 Tzeng et al.
(Continued)

FOREIGN PATENT DOCUMENTS

| GB | 2483377 A | 3/2012 |
| WO | 2012094634 A2 | 7/2012 |

OTHER PUBLICATIONS

Luo, et al ("Thickness-Dependent Reversible Hydrogenation of Graphene Layers" ACSNano, vol. 3, No. 7, 2009, pp. 1781-1788).*
(Continued)

*Primary Examiner* — Michael Maskell
(74) *Attorney, Agent, or Firm* — Kenealy Vaidya LLP

(57) ABSTRACT

Some embodiments are directed to a support for receiving a biological sample, the support comprising at least one support member, and including graphene attached to the support member. The graphene is partially hydrogenated graphene. Some embodiments are also directed to use of a partially hydrogenated graphene surface to support a biological molecule for electron microscopy. Some other embodiments are also directed to a method for making a partially hydrogenated graphene. The method includes applying a hydrogen ion or hydrogen atom to the surface of graphene. The hydrogen ion or hydrogen atom is applied at an energy in the
(Continued)

range 1 to 21 eV. A sensor comprising a surface capable of adsorbing a biological molecule thereto is also disclosed, wherein said surface includes partially hydrogenated graphene.

34 Claims, 8 Drawing Sheets

(51) Int. Cl.
   G01N 33/543 (2006.01)
   H01J 37/26 (2006.01)
   G01N 23/20 (2018.01)
   G01N 23/04 (2018.01)
   C01B 32/182 (2017.01)
   C01B 32/194 (2017.01)
   C01B 32/196 (2017.01)

(52) U.S. Cl.
   CPC .......... *C01B 32/194* (2017.08); *C01B 32/196* (2017.08); *G01N 23/04* (2013.01); *G01N 23/20025* (2013.01); *G01N 33/54393* (2013.01); *H01J 37/26* (2013.01); *H01J 2237/2007* (2013.01); *H01J 2237/2602* (2013.01)

(58) Field of Classification Search
   CPC ............. G01N 33/54393; G01N 23/04; G01N 23/20025; C01B 31/0438; C01B 31/0492; C01B 31/0484
   USPC ........................................ 250/453.11–455.11
   See application file for complete search history.

(56) References Cited

U.S. PATENT DOCUMENTS

| | | | | |
|---|---|---|---|---|
| 2013/0126865 | A1* | 5/2013 | Chiang | H01L 21/02378 257/48 |
| 2014/0044885 | A1* | 2/2014 | Boyd | C23C 16/52 427/534 |
| 2015/0235847 | A1* | 8/2015 | Beasley | H01L 21/02527 427/535 |
| 2015/0299852 | A1* | 10/2015 | Ozkan | H01G 9/20 136/255 |

OTHER PUBLICATIONS

International Search Report Written Opinion of the International Searching Authority issued in International Application No. PCT/GB2014/052423.

Apr. 30, 2014 Search Report under Section 17(5) issued in GB1318463.5.

James S. Burgess et al., 'Tuning the electronic properties of graphene by hydrogenation in a plasma enhanced chemical vapor deposition reactor', Carbon, vol. 49, Issue 13, Nov. 2011, pp. 4420-4426.

Richard Balog et al., 'Bandgap opening in graphene induced by patterned hydrogen adsorption', Nature Materials, vol. 9, Issue 4, Mar. 2010, pp. 315-319.

R. R. Nair et al., 'Graphene as a transparent conductive support for studying biological molecules by transmission electron microscopy', Applied Physics Letter—American Institute of Physics, vol. 97, Issue 15, Oct. 2010, pp. 153102.

* cited by examiner

GRAPHENE MODIFICATION

CROSS REFERENCE TO RELATED APPLICATIONS

This application is a National Phase filing under 35 C.F.R. § 371of and claims priority to International Application No. PCT/GB2014/052423, filed on Aug. 7, 2014, which claims the priority benefit under 35 C.F.R. § 119 of British Application No.: 1318463.5, and U.S. Provisional Application No.: 61/865,359, filed on Oct. 18, 2013, and Aug. 13, 2013, respectively, the contents of which are hereby incorporated in their entireties by reference.

FIELD OF THE INVENTION

The invention is in the field of supports for biological samples, such as supports for biological molecules.

BACKGROUND TO THE INVENTION

Improved electron microscopes, more stable cryo-stages and direct electron detectors with high quantum efficiency have recently brought about a revolution in biological electron microscopy (EM), enabling near atomic resolution 3D structures for large molecules and viruses[1-3]. Electron cryo-microscopy (cryo-EM) is used to determine protein structures. It is a method still under development and the resolutions of resulting 3D reconstructions have been steadily increasing. With current methodology, near-atomic resolutions can be obtained. As the resolutions increase further, the pharmaceutical industry will hope to exploit this technique, probably in parallel with x-ray crystallography, to understand how drugs bind to their protein targets. Still, grid design and preparation have remained largely unchanged since they were initially developed for electron cryo-microscopy (cryo-EM) almost three decades ago[4-6].

There are several problems with the current grids used in cryo-EM of biological specimens. First, the accumulation of electron-deflecting surface charges and beam-induced motion of samples lead to sub-optimal images[7-10]. Second, the large surface area to volume ratio of the thin water films present just prior to vitrification cause proteins to accumulate at the air-water interface, resulting in denaturation and strongly preferred orientations[5,11]. The advent of graphene and more recently graphane[12,13] allow these long standing problems to be addressed.

Currently, amorphous carbon is often used as a support for electron microscopy. Typically, thin carbon films (20-200 Å thick) are suspended over thicker layers of holey amorphous carbon which span the gaps in a typical metal mesh grid[14]. These thin carbon films are thought to decrease charging, increase particle concentration due to protein adsorption to the surface, and alter the orientational distributions of molecules.

Glow-discharging, a method using a poorly controlled plasma made by ionizing the residual air gases present after pumping a grid to mTorr pressures, makes the carbon support layer hydrophilic. This gives it adsorptive properties to help create a uniform distribution of proteins in a thin layer of ice for subsequent imaging by cryo-EM[4].

Amorphous carbon substrates have several disadvantages. First, they contribute significantly to noise in the images, especially detrimental for smaller molecules (less than 500 kDa) where the signal to noise ratio (SNR) is critical for accurate particle alignment. Second, proteins often adopt orientational preferences due to interactions with the supporting carbon, and these orientations are poorly controlled using current methods. Third, thin amorphous carbon is a poor conductor that accumulates significant mobile surface charge that can deflect the electron beam and exert strong electrostatic forces on the sample. Finally, it is difficult to control the adsorption of proteins onto the surface because of difficulties in reproducing glow discharge conditions, and because contamination builds up on the carbon surfaces dependent on their age and storage environment.

Graphene is a remarkable material, composed of a sheet of carbon atoms only one atom thick, bound together in a hexagonal lattice structure. The bonded structure is the same as in graphite, comprising a network of $sp^2$ bound carbons sharing delocalized electrons. As a result, graphene has remarkable conductive properties, and mechanical strength, making graphene an excellent support film for electron microscopy. Graphene is a mechanically robust conductor that is transparent to electrons at all spatial frequencies up to 1/2.1 Å, and is therefore a possible substrate for imaging nanoscale specimens in the electron microscope. Graphene, which may be suspended graphene, conducts charge ballistically over the sub-micron distances that span a typical hole used for imaging molecules in ice, so it is likely to significantly reduce the buildup of surface charge during electron beam exposure. In contrast, amorphous carbon is a semiconductor whose properties and conductivity ($\sim10^{-3}$ S/cm for evaporated amorphous Carbon) can vary widely depending on the conditions during deposition, which are not well controlled in the typical thermal evaporators used for their production. This makes amorphous carbon prone to surface charging and strongly susceptible to beam-induced chemical changes in its composition even at very low doses of electron exposure. Graphene's in-plane mechanical strength (Young's modulus ~1 TPa) further recommends it as a stable and robust substrate.

Despite its significant potential advantages, and ease of large-scale manufacture using chemical vapor deposition (CVD), graphene has not been widely adopted for use with biological materials. There are two main reasons for this: graphene is hydrophobic which largely precludes the deposition of proteins from aqueous solutions, and it is susceptible to surface contamination (formed during growth or adsorbed subsequently during handling and storage). Previous attempts to use graphene as a substrate for imaging biological molecules have been made, but rendering the graphene surface hydrophilic required either the use of harsh solvents that are incompatible with most proteins (DMP-30) or required conversion of the graphene to graphene oxide.

A major problem in cryo-EM is the precise control of the distribution of proteins within a thin layer of vitreous ice. During blotting and vitrification, proteins often segregate to the air/water interface or to carbon support membranes.

Graphene oxide has been used for a similar purpose[22-24] but graphene oxide presents problems since oxygen scatters electrons more strongly than carbon or hydrogen and therefore contributes nearly as much background signal as thin amorphous carbon. In addition, graphene oxide is an insulator and contains crystal defects that decreases its mechanical strength compared to pristine graphene, making it less able to neutralize accumulated surface charge and less stable as a support for thin layers of ice.

Graphene is not used with biological molecules because its hydrophobic nature precludes their reliable deposition, and because it is easily contaminated. These drawbacks mean that graphene has not been applied in EM of biological molecules or other applications involving adsorption or other attachment of biological molecules, such as sensors or similar applications.

In the unrelated field of semiconductor physics, it has been shown that exposure to a low-energy hydrogen plasma can convert graphene to graphane, its fully hydrogenated form[13,26]. Hydrogenated graphene has not been used for EM with biological samples.

The present invention seeks to overcome problem(s) associated with the prior art.

SUMMARY OF THE INVENTION

As noted above, graphene films have been used as support films for electron microscopy. However, graphene support films are not currently used for electron microscopy of biological molecules. The reason is that graphene sheets are intensely hydrophobic. This has led to insurmountable problems precluding reliable deposition of biological molecules such as proteins onto the graphene. In addition, the pristine graphene surface is easily contaminated, which renders them no better than normal amorphous carbon. Prior art attempts to render graphene usable as an EM support have led to conversion of graphene into graphene oxide. However, graphene oxide has strong electron scattering properties due to the presence of the oxygen atoms. In fact, use of graphene oxide as an EM support film contributes almost as much background signal as thin amorphous carbon. Graphene oxide has further drawbacks which include decreased mechanical strength and problems in neutralising accumulated surface charge. Thus, graphene and graphene derivatives such as graphene oxide remain no better than normal amorphous carbon for electron microscopy of biological molecules.

By contrast, the present inventors have discovered that partial hydrogenation of graphene can be useful in ameliorating the intensely hydrophobic properties of graphene. It is remarkable that this partial hydrogenation can be accomplished whilst preserving the hexagonal lattice of carbon atoms which are vital to the properties of the graphene. In addition, it is very surprising that low proportions of hydrogenation, significantly lower than full hydrogenation such as in graphane, are incredibly effective in producing a hydrophilic graphene surface which allows the reliable deposition of biological molecules.

The inventors also teach ways in which the graphene surface can be cleaned before use. The inventors teach that use of small atom plasmas (such as hydrogen or helium or neon) can be used at low energies where they will selectively remove impurities (i.e. cleaning the graphene) without harming its crystalline structure.

Thus in one aspect the invention provides a support for receiving a biological sample, the support comprising at least one support member, and comprising graphene attached to said at least one support member, characterised in that said graphene is partially hydrogenated graphene.

Suitably said graphene is 0.01% to 50% hydrogenated graphene.

Suitably said graphene is 3% to 10% hydrogenated graphene, preferably 5% hydrogenated graphene.

Suitably the graphene (partially hydrogenated graphene) of the invention has a water-graphene (air-water-graphene) contact angle in the range 68° to 90°; more suitably in the range 78° to 87°; more suitably in the range 82° to 84°; more suitably about or approximately 83°; most suitably 83°. Measurement of the contact angle is discussed in more detail below; reference is made to FIG. 1.

Suitably the at least one support member is attached to a support film, and the graphene is attached to said support film.

Suitably said support film comprises a conductive material, suitably an electrically conductive material.

Suitably said support film comprises carbon.

Suitably the support comprises a plurality of support members.

Suitably the graphene is attached to each of said support members.

Suitably the support is a sensor support.

Suitably the support is an EM support.

In one embodiment the invention related to an electron microscopy support as described above wherein said partially hydrogenated graphene comprises at least a first area of graphene and at least one further area of graphene, wherein said first area is hydrogenated to a first hydrogenation value, and said at least one further area is hydrogenated to a different hydrogenation value.

Suitably said electron microscopy support as described above further comprises a biological molecule adsorbed to said partially hydrogenated graphene.

Suitably said biological molecule is a hydrophilic biological molecule.

In another aspect, the invention relates to use of a partially hydrogenated graphene surface to support a biological molecule for electron microscopy.

In another aspect, the invention relates to a method for making a partially hydrogenated graphene, the method comprising applying a hydrogen ion or hydrogen atom to the surface of graphene, characterised in that said hydrogen ion or hydrogen atom is applied at an energy up to 21 eV, more suitably in the range 1 to 21 eV.

Suitably the energy is in the range 1 to 14 eV.

Suitably said application of hydrogen is ceased before hydrogen saturation of the graphene.

Suitably said hydrogen ion or hydrogen atom is applied in the form of hydrogen plasma.

Suitably said graphene is contacted with said hydrogen plasma for 11 to 80 seconds. Suitably said graphene is contacted with said hydrogen plasma for 18 to 22 seconds. Suitably said graphene is graphene mounted on a support. Suitably said support is an electron microscopy support.

In another aspect, the invention relates to a partially hydrogenated graphene obtained by a method as described above.

In another aspect, the invention relates to a method for cleaning a graphene surface, comprising contacting said graphene surface with a hydrogen plasma or a helium plasma or a neon plasma for a time sufficient to remove surface impurities. Suitably said plasma atoms are at an energy in the range 1 to 14 eV.

Suitably said plasma is an inert plasma. For example, said plasma is suitably composed of an inert gas, which has the advantage that it does not induce stable chemical changes in the graphene.

Suitably said plasma is neon plasma. Most suitably said plasma is helium plasma.

Suitably said graphene surface is contacted with said plasma for 1 to 30 seconds.

Suitably said graphene surface is contacted with said plasma for 1 to 10 seconds.

Suitably said graphene is partially hydrogenated graphene.

In another aspect, the invention relates to cleaned graphene obtained by a method as described above.

In another aspect, the invention relates to use of a hydrogen plasma at an energy in the range 1 to 14 eV for preparation of graphene for use in electron microscopy. Suitably the graphene is prepared by partial hydrogenation. Suitably the graphene is prepared by removal of impurities.

In another aspect, the invention relates to a method of imaging a biological sample, the method comprising:

configuring said biological sample on a support as described above, arranging said support in an electron beam of an electron microscope, and collecting image data. The image data may be image data for analysis.

In another aspect, the invention relates to an imaging apparatus operable to provide an electron microscopy image of a biological sample, said apparatus comprising: a biological sample mounted on a support as described above, an electron beam of an electron microscope arranged to be incident on said support, and a collection device operable to collect image data. The image data may be image data for analysis.

DETAILED DESCRIPTION OF THE INVENTION

Graphene is not used with biological molecules in the prior art because its hydrophobic nature precludes their reliable deposition, and it is easily contaminated.

The invention relates to the use of low-energy hydrogen plasma to modulate the surface properties of graphene, without degrading the graphene lattice. This alters the properties of graphene to allow the deposition of proteins onto its surface and precisely control their distribution. In addition, it cleans the graphene surface by non-destructively removing contaminants. Thus the invention can be used to precisely control the distribution of proteins on a graphene surface. We demonstrate its usefulness in imaging and three-dimensional reconstruction using single particle electron cryo-microscopy. The invention is also useful in other biological applications involving the controlled adsorption of viruses, proteins or other biological molecules onto graphene such as a graphene surface. These applications include graphene-based sensors, for example sensors for detecting the presence, concentration and/or other properties of molecules in contact with the graphene surface.

We teach use of low-energy hydrogen plasma to modulate the surface properties of graphene, without degrading the graphene lattice. This alters the properties of graphene to allow the deposition of proteins onto its surface and precisely control their distribution. This also cleans the graphene surface by non-destructively removing contaminants.

We teach low-level hydrogenation of graphene with a low-energy hydrogen plasma that can address the prior art problems described above: removal of surface contamination and/or making graphene suitably hydrophilic for use as a substrate for biological molecules such as proteins. By using a hydrogen plasma whose energy is well below the sputter threshold for graphene, we observe no significant damage to the suspended lattice. Moreover, we are able to tune protein distribution on graphene where hydrogen plasma dose is directly related to the surface density of proteins. This is particularly advantageous for EM applications such as cryo-EM applications, and/or sensor applications such as biosensor applications.

Electron microscopy of biological samples is typically operated over a resolution of 1/1.5 Å to 1/500 Å. Since substrates such as graphene have an effective minimum resolution of approximately 1/2.1 Å, they may be regarded as "invisible" for study of biological molecules.

We demonstrate the use of this method in electron microscopy by determining a 3D reconstruction of 70S and 80S ribosomes imaged on hydrogen plasma treated graphene.

We show that the partial hydrogenation of a graphene lattice can induce adsorption of proteins from an aqueous solution, enabling control of particle surface density independent of other variables. In cryo-EM sample preparation, other variables might include humidity, blot time, etc. By tuning their adsorption to the graphene, we solve problems of the prior art associated with protein aggregation and denaturation at air/water interfaces. We show that partially hydrogenated graphene reduces the problems associated with amorphous carbon including irreproducibility, charging and increased background noise.

Further, we show that a low-energy hydrogen plasma can selectively remove surface contaminants much faster than it can reduce the graphene lattice itself. This advantageously allows removal of impurities (cleaning) whilst avoiding or minimising further changes to the hydrogenation state of the graphene.

Graphene, as treated with a low-energy hydrogen plasma, is a reproducible and tunable surface for the adsorption of proteins. On this basis, we envision that the preparation of biological specimens for electron microscopy will move from a trial-and-error art to a systematic process of screens of surface conditions without compromising the structural integrity of the proteins or the quality of the images.

In addition the invention provides advantages in cryo-EM such as increased stability of ice, and/or decreased motion of particles—these are discussed in more detail below.

Importantly this method depends on the notion of an energy threshold for the graphene lattice where the plasma is controlled as taught herein so that energetic ions within the plasma have insufficient energy to directly remove atoms from or damage the graphene lattice. Thus the only modification that can occur to the graphene lattice is via chemical reaction with the species of the plasma. The threshold energy for direct removal of a carbon atom from a graphene lattice has been established at around 21 eV.

Suitably plasmas well below this energy are used to ensure there is no sputtering of the graphene.

In the examples we demonstrate the invention using hydrogen for cleaning. However, other ion species whose energy is insufficient to remove a carbon atom from the graphene lattice via a direct recoil event will also be useful since their action too will be limited to chemical reaction with the surface as explained for hydrogen. These will include for example helium, such as helium in the 5-10 eV range. Helium is of particular interest because it will not react with the graphene surface but will remove contamination.

Prior art attempts to render hydrophobic graphene as usable for electron microscopy have involved very harsh treatments. In some instances, the graphene has been converted to graphene oxide. Graphene oxide has a number of drawbacks which include its behaviour as an insulator, problems in neutralising accumulated surface charge, and reducing mechanical strength/stability as support for thin ice layers needed for cryo-EM.

The prior art has failed to render graphene usable as a substrate for EM study of biological molecules.

It is a key advantage of the invention that through the choice of atoms/conditions which are used to treat the graphene, it can be modified chemically whilst being physically unaltered. In other words, the inventors are able to change the bond structure within the graphene, but not remove atoms from the graphene lattice which would disrupt its physical properties vital to its use in EM.

The inventors teach that even very low proportions of hydrogenation (such as 0.1 to 20% hydrogen per carbon) can be enough to restore sufficient hydrophilicity to permit reliable deposition of biological molecules onto the surface for EM.

In the field of material science, a substance called graphane has been produced. Graphane is a fully hydrogenated carbon sheet. In graphane, each carbon is sp³ bonded to 3 carbons, plus a hydrogen. By contrast, the inventors teach the partial hydrogenation of graphene. In this way, the characteristics of graphene are preserved, whilst advantageously providing enough hydrogenation to permit distribution of biological molecules across the graphene surface, facilitating excellent results in EM studies. It is an advantage of the invention that the lattice structure is completely preserved. Without wishing to be bound by theory, of course the precise bond lengths of the hydrogen-bonded carbons in the partially hydrogenated graphene of the invention may vary compared to the bond lengths of entirely unhydrogenated graphene. However, what is important is that the hexagonal lattice structure of the graphene is preserved according to the invention.

In the course of this study, it was discovered to be very surprising that hydrophilicity can be saturated for the partially hydrogenated graphene sheet at far lower hydrogenation values than might have been expected. Before this work, it would be expected that hydrophilicity would reach saturation at 100% hydrogenation (i.e. graphane). However, according to the data presented herein, hydrophilicity is in fact at or near saturation at approximately 20% hydrogen.

Although certain substances such as graphene or graphane have been placed under electron microscopy in the prior art, it is important to note that these have mainly been studies in the field of materials science. Graphene is of interest to materials scientists in the field of electronics, because graphene films may be grown by chemical vapour deposition for use in semiconductor computer chips. Due to the interest in conductive properties of graphene, it has been studied in the field of materials science as a possible future competitor for classic semiconductors such as silicon. In these studies, graphene has been combined with electron microscopy purely as a sample to be studied. Some new materials which have been produced have been subjected to EM in order to discern their structure. There has been no teaching of partially hydrogenated graphene as a support substrate for biological samples such as biological molecules anywhere in the art. This is a contribution directly made by the present invention.

In a broad aspect the invention relates to a partially hydrogenated graphene comprising a biological molecule adsorbed thereto.

Cleaning of Graphene Sheets

The inventors have studied the threshold effects of treating graphene with the small atom plasmas as described herein. It is of considerable interest that cleaning effects can be observed well before hydrogenation takes place. Without wishing to be bound by theory, it is believed that the highly energetic small atoms in the plasma used to treat graphene can easily disrupt and remove contaminants from the surface of the graphene at far lower energies and/or at far shorter timescales than would be required for chemical reactivity (such as hydrogenation) of the graphene. Therefore, by using lower energy or shorter timescale treatments of the graphene with small atom plasmas, an effective decontamination or cleaning of the graphene can be effected without altering the chemical or physical makeup of the graphene sheet.

Suitably the plasma is hydrogen, helium or neon plasma. Suitably the plasma is an inert plasma such as helium or neon plasma. Suitably the plasma is neon or helium plasma. Suitably the plasma is neon plasma. Most suitably the plasma is helium plasma.

Helium plasmas are suitable for treatment of graphene such as graphene sheets according to the invention. Helium plasmas are suitably used with ions striking the surface with energies up to 21 eV, more suitably in the range 1 to 21 eV, more suitably 1 to 14 eV, more suitably 14.0 eV or less, most suitably 5 to 10 eV.

Hydrogen plasmas are especially suitable for the treatment of graphene such as graphene sheets according to the invention. Hydrogen plasmas are suitably used with ions or atoms striking the surface with energies up to 21 eV, more suitably in the range 1 to 21 eV, more suitably 1 to 14 eV, more suitably 14.0 eV or less.

Neon plasmas may be used to treat graphene according to the invention. When using neon plasmas, lower energies are more desirable due to the larger size of the neon atoms. In this regard, special attention must be paid to the plasma sheath voltages and the ultimate energy of the ions striking the surface so that damage to the graphene is avoided whilst still maintaining the neon in a plasma state.

Argon plasma is much less likely to be useful in the cleaning of graphene except at very low energies and/or exposure times, since the large size of argon atoms risks damage to the graphene lattice.

Energy Selection for Non-Destructive Cleaning of Graphene

For low-energy ions and atoms the maximum transmitted energy, $T_{max}$, in a single collision is $$T_{max} = \frac{4 \, mM}{(m+M)^2} E$$

Where m is the mass of the ion/atom in the plasma M is the mass of the target atom, in this case carbon, and E is the energy of the ion/atom in the plasma. So for neon striking carbon we have $$T_{max} = \frac{4(20.1 \, amu)(12.0 \, amu)}{(20.1 \, aum + 12.0 \, amu)^2} E = 0.936 E$$

So if we want $T_{max} < 21$ eV then the energy of the ions striking the surface of the graphene should be $$E_{max} = \frac{T_{max}}{0.936} = 19.7 \text{ eV}$$

Or for $T_{max} < 14.1$ eV then $E_{max} < 13.1$ eV

However, the actual energies of particles in a plasma will comprise a distribution of energies which generally follow Boltzmann statistics. In addition, at the edge of the plasma near a surface there is often a region which is depleted of electrons called the plasma sheath. This sheath comprises an electric field that can accelerate ions from the plasma into the surface of the sample with appreciable (several eV) energies. So to ensure minimal or no damage the operator should suitably choose a plasma temperature (Energy) and configuration such that the atoms and ions that strike the surface of the graphene well below the $E_{max}$ value from above; choosing a lower energy has the advantage that there will be very few ions/atoms in the high energy tail of the distribution of energies that exceed the threshold $T_{max}$.

Thus, taking into account the guidance above, the skilled worker can select appropriate energies and plasma configurations according to the present invention. For example, when using neon, an energy of 5-10 eV would be optimal.

Similar calculations can be done for other atoms (atom plasmas) such as H, He, Ne, F, N. Most suitably the plasma used in the invention is H, He or Ne.

For cleaning graphene aspects of the invention, suitably He, Ne and/or other noble gasses are used—these have the advantage of permitting removal of contaminants (i.e. cleaning the graphene) without chemically modifying the graphene.

Thus the most suitable plasma energy for neon is 5 to 10 eV.

Without wishing to be bound by theory, the main consideration in suitability of an atom for plasma treatment in the current invention is the energy of the atomic (not electron) species which strike the surface of the graphene and their ability to chemically modify the graphene lattice. In particular, larger atoms require greater energies to maintain them in a plasma state. At these greater energies, there is a risk of exceeding the threshold for removal of a carbon atom from the graphene sheet. Any plasma containing atoms energized above the level required for removal of a carbon atom from the graphene sheet is unsuitable for use in the present invention. Plasmas containing oxygen are also apt to react chemically with the lattice, thus converting it to graphene oxide or destroying it completely, both of which are undesirable for the present invention, thus plasmas containing oxygen are unsuitable for use in the present invention.

Most suitably, the plasmas according to the invention are neon or helium or hydrogen plasmas. Most suitably, the plasmas according to the invention are helium or hydrogen plasmas. Preferably hydrogen plasmas are used for tuning or hydrogenation of the graphene. Preferably hydrogen or helium or neon plasmas are used for cleaning or removing impurities from the graphene, most suitably helium plasmas are used for cleaning or removing impurities from the graphene.

For cleaning or removing impurities from the graphene suitably said graphene is contacted with said plasma (such as hydrogen plasma or helium plasma or neon plasma) for 1 to 30 seconds, preferably for 1 to 10 seconds.

This cleaning effect is achieved by the chemical reaction by energetic species in the plasma with the contaminant molecules on the surface of the graphene, thereby volatilising them and causing their removal.

'Clean graphene' or 'cleaned graphene' is regarded as clean or cleaned as follows: 'clean'=mass of contaminants/unit area <mass of graphene/unit area/100 OR surface area of contaminants <surface area of graphene/100; more suitably 'clean'=mass of contaminants/unit area <mass of graphene/unit area/1000 OR surface area of contaminants <surface area of graphene/1000.

Hydrogenation

Hydrogenation of the graphene may be accomplished by any suitable method known in the art. Most suitably, hydrogenation is done by treating with a hydrogen plasma. However, it may equally be accomplished by using an ion beam to deliver hydrogen atoms to the graphene surface. The key teaching is to apply hydrogen ion or hydrogen atom to the surface of the graphene at the correct energy level.

Graphene Crystal Grain Boundaries

Regarding the energy levels, the maximum energy levels which should be used according to the invention are 21 electron volts (eV). At energy levels exceeding 21 eV, there is a likelihood that carbon atoms may be knocked out of the graphene lattice. Clearly, this is highly undesirable since it would disrupt the important lattice structure of the graphene. For this reason, energies of atoms or ions striking the lattice of 21 eV or lower are preferred.

A single sheet of graphene is often made up of a patchwork of multiple graphene crystals. At the grain boundaries between these crystals there are alternate bonding arrangements known as "5-7 defects" (sometimes called "Stone-Wales defects"). The carbon atoms in the 5-7 defects are still $sp^2$ bonded, but the energies for their removal are lower than the 21 eV specified above due to these edge defects in the bonding pattern. It is possible to disrupt these edge defect carbon atoms with energies as low as 15 eV. Therefore, suitably according to the invention, ion energies of 14 eV (such as 14.0 eV) or lower are advantageously employed. This is especially advantageous when the region of graphene to be treated includes a grain boundary.

In general, lower energy plasmas can be harder to maintain. Thus, notwithstanding the need for lower energy levels in order to avoid disruption of the carbons in the graphene lattice, suitably energy levels are as high as is possible whilst safely avoiding destruction of the graphene lattice. This provides the advantage of easier management/maintenance of the plasmas being used for treatment. This also provides the advantage of shorter exposure times.

Suitably, plasma energies for hydrogenation are in the range 1 eV to 14 eV.

Suitably plasma energies for hydrogenation are <14 eV. Suitably, plasma energies for hydrogenation are in the range 1 eV to <14 eV.

For hydrogenation, for example using the commercially available apparatus as described below, suitably said graphene is contacted with a hydrogen plasma for 11 to 165 seconds, suitably 11 to 120 seconds, suitably 11 to 80 seconds, suitably 11 to 40 seconds, suitably 15 to 25 seconds, suitably 18 to 22 seconds, most suitably 20 seconds. These values are particularly advantageous for ribosome adsorption; 20 seconds is particularly advantageous for this application and provides the specific advantage of especially uniform distribution of the molecules being studied such as ribosomes.

Suitably said graphene is contacted with a hydrogen plasma for 10 to 40 seconds.

Making and maintenance of plasmas is routine for a skilled worker and can be accomplished using commercially available plasma generators.

Without wishing to be bound by theory, low-energy plasmas can have differing densities and their geometry and electrical control of the sample and chamber walls and generation method can strongly affect the number of 'strikes' by an electron or ion per unit time, per unit area, as well as the energy of the ions or electrons. This is sometimes referred to as the 'dose' of (e.g.) hydrogen administered. Thus, density of the plasma or other factors as noted above can affect the 'dose' of hydrogen applied per unit time. Therefore, for a given density of plasma, increased time of exposure leads to increased dose. The timing of the treatments with plasmas as taught herein provides exemplary dosing as demonstrated. If a person skilled in the art uses plasmas of differing densities energies or electrical, it is well within their capabilities to adjust the timing accordingly to achieve the levels of hydrogenation or cleaning as taught herein. If any further guidance is required, the levels of hydrogenation of the treated graphene (partially hydrogenated graphene) can simply be assessed or estimated as taught herein (for example via contact angle measurements or diffraction measurements of changes in graphene lattice parameters) and the 'dose' adjusted to achieve the desired level of hydrogenation.

Advantages

It is a key advantage of the invention that adsorption of biological molecules such as proteins onto graphene is facilitated. In other words, it is an advantage of the invention that the deposition of protein onto the graphene surface can now be controlled.

Once the partially hydrogenated graphene EM support has been made, it is treated or used exactly as for any other graphene EM support. For example, the cryo-EM samples may be prepared by standard robotic techniques.

Partially hydrogenated graphene supports may be made by partially hydrogenating a graphene sheet, or may be made by preparing partially hydrogenated graphene and then arranging it onto supports. Whichever way these are manufactured is typically a matter of operator choice. It may be advantageous to prepare graphene support(s) and then partially hydrogenate them to the required degree, thereby avoiding issues of contamination, which might arise during transfer of partially hydrogenated graphene onto the bars or walls or periphery of the support. Thus, in one embodiment it is preferred to clean or to partially hydrogenate the graphene when present on an EM support.

We teach use of hydrogenated graphene to precisely control the distribution of biological molecules such as proteins in ice. Proteins adsorbed in this way retain their structural integrity as verified by three-dimensional reconstructions of the 70S & 80S ribosomes (see examples). The invention enables the systematic screening of surface conditions for protein adsorption, and addresses the most poorly controlled aspect of sample preparation for biological electron microscopy.

In addition, we track individual ribosomes in ice and find their beam-induced motion is advantageously reduced nearly five-fold on partially hydrogenated graphene according to the present invention. Strengthening ice-embedded particles with a partially hydrogenated graphene support improves both sample preparation and image quality in biological electron microscopy. Thus, we demonstrate that hydrogen plasma treated graphene improves cryo-EM images by substantially reducing beam-induced motion.

The invention provides the advantage of reducing sample motion. The invention provides the advantage of increased image quality.

Other Applications

Biosensors are known which involve a transistor whose gate is designed to be in contact with a fluid. Such a device is configured such that when a particle of interest comes near the gate, the conductive properties of the transistor are altered, allowing a signal to be read out. The entity binding to the sensor (i.e. being detected) can be any small particle of interest, for example proteins, virus particles or any other small moiety of interest.

Using tuneable graphene according to the present invention, such as partially hydrogenated graphene, it is possible to produce a transistor-type biosensor which changes its conductive properties according to whether or not the moiety of interest (e.g. protein, virus particles or other entity) is or is not bound. A key benefit provided by the invention is the ability to create and/or tune a surface for the specific binding of particle using a material (graphene) which is ideal for integrating in such transistor type devices.

Detectors (sensors) for molecules such as biological or chemical molecules may be produced according to the present invention. For example, partially hydrogenated graphene may be used in the production of sensors such as biosensors using partially hydrogenated graphene as the sensitive element, for example as a sensitive planar element in a nanoscale field-effect device.

Such devices may be made using semiconductor nanowires (described in Refs. 46-48), carbon nanotubes (described in Ref. 49), or graphene (described in Refs. 50-51). According to the present invention the sensitive element in the sensor (e.g. system) comprises partially hydrogenated graphene, such as a region of partially hydrogenated graphene. Such a sensitive element is typically constructed to be in contact with the sample such that when a particular molecule binds to the surface, or binds to one or more molecules bound to the surface, the electronic properties of the partially hydrogenated graphene change. This change in electronic character can then be read out as an electrical signal from the device. For example, the invention may relate to a device to detect single viruses such as described in Ref. 47 by substituting the silicon nanowire of Patolsky with partially hydrogenated graphene of the invention.

In another embodiment, the invention provides a sensor for cancer biomarkers such as Prostate Specific Antigen (PSA) where antibodies to the biomarkers are bound to partially hydrogenated graphene. In this embodiment the sensor may be constructed as described in Ref. 52, substituting partially hydrogenated graphene of the invention into the sensitive/conductive part of the sensor arrays e.g. by replacing or augmenting the nanowires with partially hydrogenated graphene.

In another embodiment Ca2+ may be detected by Calmodulin for example as described in Ref 46; in this embodiment the Calmodulin may be coupled to, such as bound to, partially hydrogenated graphene (instead of, or in addition to, the nanowires of Ref. 52).

Many other sensor applications may be performed by the skilled person using partially hydrogenated graphene according to the teachings provided herein. Unlike the silicon nanowires that have been used in known biosensors, graphene (e.g. partially hydrogenated graphene according to the present invention) offers the advantage of extraordinary levels of electronic sensitivity and may allow the detection of even single binding events of small molecules to individual proteins. The use of partially hydrogenated graphene allows specific control of biological molecule adsorption such as protein adsorption to graphene-based sensors, thereby enabling a large multitude of possible detection strategies. Further, since the methods of the invention (such as the plasma process) are easily amenable to large-scale fabrication on a single device or chip, the invention enables fabrication of a plurality of such sensors tuned to detect specific molecules.

Suitably sensors of the invention are biosensors.

In another aspect, the invention relates to a sensor such as a biological sensor, where the sensitive element of the sensor comprises partially hydrogenated graphene. Suitably the partially hydrogenated graphene is obtained by a method as described above.

In another aspect, the invention relates to a sensor comprising a surface capable of adsorbing a biological molecule thereto, wherein said surface comprises partially hydrogenated graphene.

Suitably said graphene is 0.01% to 50% hydrogenated graphene.

Suitably said graphene is 3% to 10% hydrogenated graphene, preferably 5% hydrogenated graphene.

In another aspect, the invention relates to a sensor comprising a support as described above.

The invention finds application in these and other uses which exploit the tuneable properties of the graphene produced as described herein. The key advantage is that the inventors now teach a method of controlling adsorption of hydrophilic molecules (such as protein) onto the graphene surface, which may be exploited in any number of ways according to operator choice.

Tuning of Graphene Surface

Biological sample means any sample from, or derived from, an organism. The sample may be a crude sample or a purified or partially purified sample. The sample may be a fluid such as a body fluid, for example blood, serum, plasma, cerebrospinal fluid, saliva, semen, urine or any other body fluid. The sample may even comprise whole organisms such as bacteria, viruses or other microscopic organisms. The sample may comprise cell(s) from an organism. The sample may comprise one or more biological molecule(s) extracted or purified from an organism, such as described below.

Suitably the sample is an in vitro sample.

Biological molecules means molecules produced by living organisms such as proteins, nucleic acids, carbohydrates or lipids. Suitably biological molecules are proteins or protein complexes. Suitably biological molecules are hydrophilic biological molecules. Binding of proteins or other biological molecules to the graphene surface can vary according to the charge state, hydrophilicity/hydrophobicity of the moiety binding, or on the salt/buffer/solvent conditions prevailing. It is an advantage of the invention that the hydrophilicity of the graphene surface can now be tuned by adjusting the proportion of hydrogenation of the surface.

Suitably the biological molecule is an in vitro biological molecule.

Hydrogenation values may be expressed as % hydrogenation. This means the proportion of $sp^2$-bonded carbon atoms converted to $sp^a$ H-bonded carbon atoms. In other words, it is a measure of what proportion of the carbon atoms in the graphene sheet have accumulated an associated hydrogen atom. If every carbon atom was H-bonded, this would be 100% hydrogen saturation (graphane); if no carbon atoms were H-bonded this would be 0% hydrogen saturation (graphene); the invention is concerned with values greater than 0% and less than 100%, i.e. partially hydrogenated graphene.

Hydrogenation may be measured by any suitable means known in the art. Exemplary techniques for assessment of hydrogenation are demonstrated in the examples. For example, hydrogenation may be estimated by measuring the water-graphene contact angle as demonstrated in FIG. 1. In this case the 20 second hydrogen plasma exposure time corresponds to approximately 5% hydrogenation; the 80 second hydrogen plasma exposure time corresponds to approximately 20% hydrogenation and so on. Similarly, with reference to FIG. 3, the 20 second hydrogen plasma exposure (FIG. 3c) is approximately 5% hydrogenation; the 40 second hydrogen plasma exposure (FIG. 3d) is approximately 10% hydrogenation and so on. Alternatively the hydrogenation may be estimated by calculating the graphene-water interfacial energy as below.

Calculation of Graphene-Water Interfacial Energy

For a liquid droplet in a gas environment on a solid surface, the liquid-solid interfacial energy, W, is related to the equilibrium contact angle between the droplet and the surface, by the Young-Dupré equation:

$$W=\gamma_w(1-\cos\theta)$$

where $\gamma_w$ is the water surface tension, 72 mJ/m², (ref 44). Using the contact angle values from the as grown graphene sample ($\theta_{gr}$=91±1.7°) and the saturation value from the exponential fit to the data, ($\theta_{grh}$=66±1.3°) the change in surface energy due to the hydrogen plasma treatment is then just the change in the interfacial energy for the two surfaces:

$$\Delta W=\cos\theta_{gr}-\cos\theta_{grh}$$

which for the values measured is −0.19±0.02 eV/nm². While the presence of the copper substrate may cause a small reduction in the measured angle for native graphene[45], it will have negligible effect on the change in angle used to calculate the change in interfacial energy as the substrate will have the same effect on all the measurements.

Alternatively change in the lattice constant (the average distance between carbon atoms in the lattice) may be measured as an assessment of hydrogenation of the graphene. This may be done for example using electron diffraction, for example carried out as described with reference to the figures such as FIG. 6 herein.

Surprisingly low levels of hydrogenation were enough to facilitate adsorption of hydrophilic molecules to the partially hydrogenated graphene surface, such as 0.1 to 20% hydrogenation.

Suitably partially hydrogenated graphene of the invention may comprise 0.01 to 50% hydrogen per carbon; or may contain 0.01 to 10% hydrogen per carbon; or may contain 1 to 10% hydrogen per carbon; or may contain 3 to 10% hydrogen per carbon; or may contain 3 to 5% hydrogen per carbon.

| Hydrogenation of graphene | Applications/Advantages |
| --- | --- |
| <0.01% | cleaning of surface contaminants |
| 0.01-1% | facilitate adsorption of hydrophilic molecules |
| 0.01-50% | adsorption and/or detection of large complexes e.g. viruses or cells. |
| 20% | saturation of hydrophilicity |
| 5% | optimum for adsorption of ribosomes such as 70S & 80S ribosomes |
| $10^{-4}$-0.01% | adsorption of hydrophobic molecules, for example lipids or membrane proteins |

Patterned Graphene

Advantageously, different degrees of hydrogenation may be provided at different spatial locations (areas) within the same physical graphene sheet. This may be accomplished by masking the different areas of the sheet during hydrogenation so that some areas are hydrogenated to a higher degree, and other areas are hydrogenated to a lower degree. Ideally, it may be desirable to produce a graphene EM support having a high hydrogenation value at one end, and withdrawing the masking during the hydrogenation process so that the opposite end of the same graphene support is left with a low hydrogenation value. In this manner, the optimal hydrogenation value may be determined for particular biological molecules which are intended to be deposited on the graphene surface. These graded graphene supports with variable hydrogenation are especially useful in calibration or selection of optimal hydrogenation levels for the partially hydrogenated graphene of the invention.

The masking during hydrogenation may be accomplished by any suitable means known in the art. For example, the use of an electrode near the graphene may be employed which shelters or deflects the hydrogen atoms away from the graphene surface whilst it is in place. Such an electrode may be withdrawn across the graphene surface (e.g. just above the graphene surface) over a particular time course, so that the graphene which is exposed first will enjoy the longest hydrogenation treatment (and therefore the highest degree of hydrogen saturation), and the area of graphene which is masked for longest will enjoy the lowest exposure to hydrogen (and therefore the lowest hydrogen per carbon value). Alternatively, more than one electrode could be employed to establish a field across the graphene such that ions impinging on the surface are retarded more near one electrode than another. Thus, a gradient in dose across the graphene substrate might be advantageously achieved without the need to apply a masking material directly to the graphene surface.

Optionally a directional beam of hydrogen ions may be used to apply varying amounts of hydrogenation to different regions or areas of the same graphene sheet in order to create patterned graphene.

In one embodiment different areas (spatial locations) on the graphene are hydrogenated to different levels or values.

In one embodiment the graphene may be graded evenly from a first hydrogenation value at one location on the graphene to a second (different) hydrogenation value at a second location on the graphene.

Suitably, the EM supports of the invention do not comprise graphene oxide.

Suitably, the EM supports of the invention do not comprise graphane.

Graphane is not graphene. Graphane is a fully hydrogenated carbon sheet. The carbons in a graphane sheet each bond with a hydrogen. In other words, the ratio of carbon to hydrogen in graphane is 1 to 1—every carbon atom present has an associated hydrogen atom. This is full or complete (100%) hydrogen saturation. This substance is graphane. The present invention is concerned with partially hydrogenated graphene. Partially hydrogenated means less than 100% (i.e. less than 1 to 1) saturation of the carbon atoms with hydrogen atoms. The partially hydrogenated graphene comprises carbon atoms which are not bonded or associated with hydrogen atoms. Hence, partial hydrogenation should have its normal meaning in the art. Partially hydrogenated graphene has at least some of the carbon atoms associated with bonded hydrogen atoms, but not all of them. It is the surprising properties of this intermediate partially hydrogenated graphene substance upon which the invention is based.

Support Construction

Suitably the support is an electron microscopy support or a sensor support such as a biosensor support. Most suitably the support is an electron microscopy support.

An electron microscopy support is an apparatus which allows the carriage of the sample to be examined by electron microscopy into and out of the electron microscope. A degree of mechanical strength is provided to the support by the peripheral wall or rim or members (such as bars) of the support. The sample to be examined is mounted onto the support within an area defined by the periphery of the support. The sample itself is typically mounted onto a lattice or film which is carried by the support.

The lattice or film part of the support typically has a mesh or "holey film" structure. These films are typically described in the art with two numbers, for example "2/1"—this means a foil with two micrometre pores or holes at a one micrometre spacing. Similarly, a foil designated 2/4 would have holes or pores of two micrometres, at a spacing of four micrometres, and so on.

Suitably, said support members are bars. Suitably, said support bars are arranged in a grid. Sometimes the EM support is referred to as an EM grid.

The support film may be referred to as a support foil.

Suitably, the graphene is hydrogenated when mounted on an electron microscopy support.

Suitably, the graphene surface being cleaned is the surface of graphene mounted on an electron microscopy support.

When a graphene support is described for use in electron microscopy, for example electron microscopy of biological molecules, this has its normal meaning in the art. In particular, "for" use in EM means "suitable for" use in EM. An experimental graphene sheet in the field of semiconductor science is not "suitable for" EM of biological molecules, unless it had been formed into an arrangement which could genuinely be used for that application.

Suitably, the support is dimensioned for EM applications.

Dimensioned for EM applications may mean 3 mm diameter grid.

Suitably, the support is configured to accept a thin layer of vitreous ice. Suitably, the support is conductive.

Suitably, the support is, or is adapted to be, operably connected to an electrical control apparatus, for example to facilitate charge dissipation during EM.

Suitably, the support is adapted to enable robotic handling and/or robotic sample preparation for EM.

Suitably, the support is sealed in a vacuum chamber.

Suitably, the support is sealed in a protective environment, for example to facilitate transport or storage.

Suitably, the support is packaged for mechanical protection during transport and/or handling.

In some embodiments the support may comprise aluminium or stainless steel or titanium.

Suitably, the support comprises one or more of molybdenum, gold, copper or nickel. Most suitably the support comprises gold.

Suitably, the support is silicone-free.

The graphene sheet may be applied to either side or both sides of the support.

When the support comprises a layer of holey carbon, for example a layer of holey carbon on a gold grid, suitably the graphene is applied to the holey carbon side.

Suitably, the support may comprise one or more mechanical markers, such as a cut-out, at the periphery of the support. This has the advantage of assisting in orientation of the support.

Suitably, the support is a Quantifoil™ grid.

Suitably, the support comprises a perforated support film. Suitably the perforated support may have one or a plurality of holes. Suitably the perforated support has a predefined hole size.

Suitably the support film is mounted on the wall or rim or bars of the support itself.

Holes may be of any shape. Suitably, the holes may be circular or square.

Suitably, the holes may be arranged in a regularly repeating pattern.

Suitably, hole sizes are determined by operator choice.

Suitably holes used in support film(s) have dimensions 0.05-10 um.

Most suitably when the support film comprises amorphous carbon the dimensions of the holes used are in the range 0.05-10 um.

Suitably, bar widths are determined by operator choice.

Suitably, the support film is a solid, electrically conductive thin film.

Suitably the support film is 100-500 Angstrom thick.

Suitably the support film comprises amorphous carbon.

Suitably the support film comprises 100-500 Angstrom thick layers of amorphous carbon support film.

Suitably the support may comprise irregular holes in a carbon film, 'homemade' carbon film, or perforated film(s) from other sources.

Suitably, the support film is a carbon film.

Most suitably, the support comprises a holey carbon support film on a 300 mesh gold grid, such as produced by Quantifoil Microtools GmbH of Jena, Germany.

Further particular and preferred aspects are set out in the accompanying independent and dependent claims. Features of the dependent claims may be combined with features of the independent claims as appropriate, and in combinations other than those explicitly set out in the claims.

Where an apparatus feature is described as being operable to provide a function, it will be appreciated that this includes an apparatus feature which provides that function or which is adapted or configured to provide that function.

Further Applications

Graphene tuned by partial hydrogenation to interact with biological molecules can be used in a range of applications including graphene-based sensors.

The invention finds particular application in electron microscopy (EM), such as cryo-EM. In particular, the invention is especially useful in electron microscopy of biological molecules.

The methods of the invention can be used to precisely control the distribution of proteins on a graphene surface such as a suspended graphene surface. We demonstrate its utility in imaging and three-dimensional reconstruction using single particle electron cryo-microscopy. It will be apparent that the methods of the invention may be used for other biological applications involving graphene.

Graphene-based supports (grids) produced according to the invention find application in industry such as manufacture, sale and use of said supports.

Methods of the invention find application in the production and/or cleaning of graphene products.

The invention finds application in the manufacture of graphene-based devices and sensors, as well as in cleaning graphene in the non-destructive manner taught herein. The invention may be used in production of arrays of graphene sensors whose surfaces are tuned to interact with specific proteins or biological molecules for detection or assay. The invention provides a direct and highly scalable means to accomplish this.

We provide the ability to specifically tune the graphene surface to interact with proteins. This means that any sensors or devices that depend on the interaction of graphene with proteins can be designed for a particular application.

BRIEF DESCRIPTION OF THE DRAWINGS

Embodiments of the present invention will now be described further, with reference to the accompanying drawings, in which.

Figure 6:
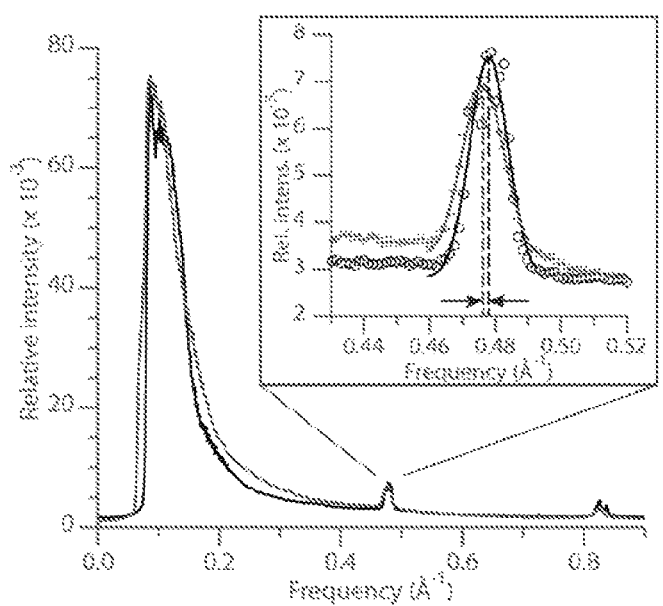

Plot a shows the air-water-graphene contact angle versus exposure time, with insets containing examples of optical micrographs used to measure the angles. The curve is an exponential fit to the data with rate constant of $1/56$ seconds. Error bars are the std. dev. of 3-5 measurements at each dose in y and the estimated accuracy of the exposure time, ±1 second, in x. Diffractograms (b-d): selected area electron diffraction patterns for the same suspended graphene sample before hydrogen plasma exposure (b) after 20 seconds (c) and 40 seconds (d). Arrow points to the 0-110 reflection at 2.14 Å and sets the scale for all three diffractograms. The change in the lattice constant for c & d relative to b is less than the error in the measurement, ≈0.9% (FIG. 6).

Figure 2:
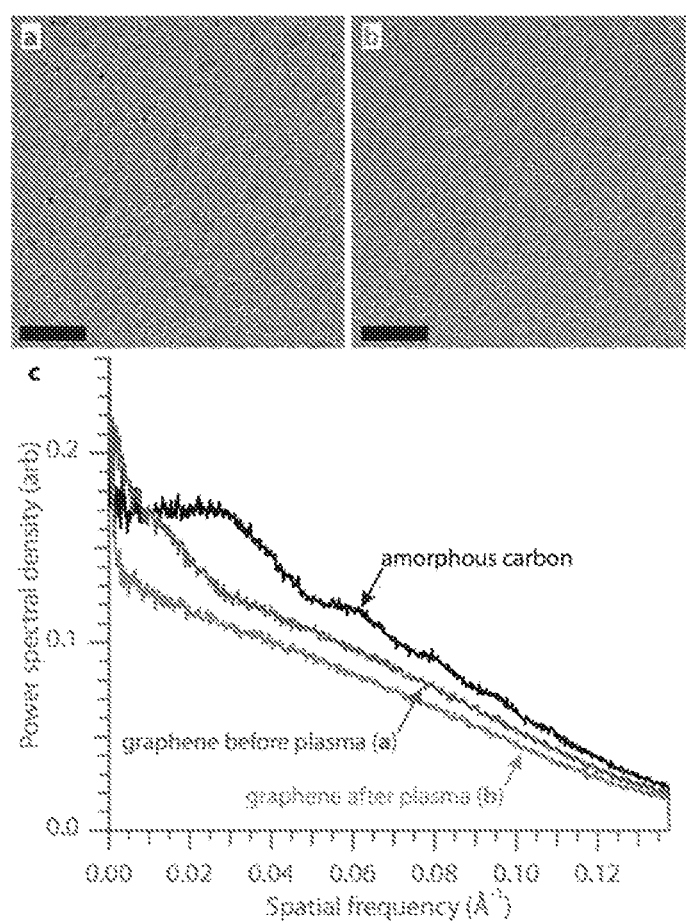

FIG. 2 shows electron micrographs of suspended graphene before (a) and after (b) 30 second hydrogen plasma treatment. Scale bars are 1000 Å, nominal defocus is -2.0 μm and dose is 25 e-/Å$^2$. Plots in c show the power spectrum in each complete micrograph (FIG. 7*a-c*), normalized to the total image intensity in each micrograph, where upper black curve is for 28±1.4 Å thick amorphous carbon, red curve (a) is graphene before plasma (image a), and blue curve (b) is graphene after plasma (image b).

Figure 3:
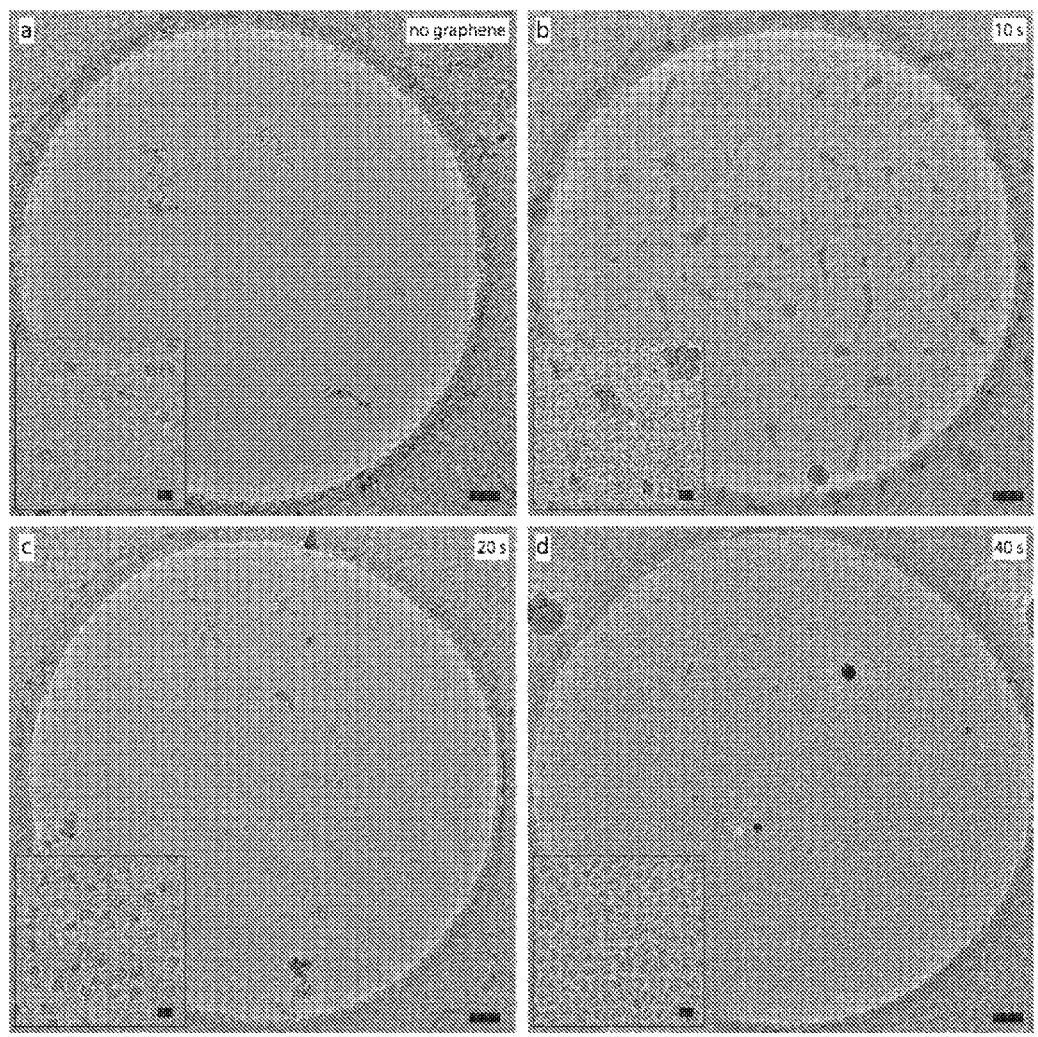

FIG. 3 shows images of ribosomes on hydrogen plasma treated graphene. Panels a-d show electron micrographs of 70S ribosomes in vitrified ice at 80 K. Panel a is a standard Quantifoil grid treated with a 10 s H plasma dose. Panels b-d are Quantifoil grids covered with monolayer graphene, and treated with 10, 20 and 40 s of H plasma, respectively. All other blotting and vitrification conditions are the same for all four samples. Insets are enlargements of selected regions from each image, showing the typical distribution of particles. Scale bars are 1000 Å for main images and 200 Å for insets.

Figure 4:
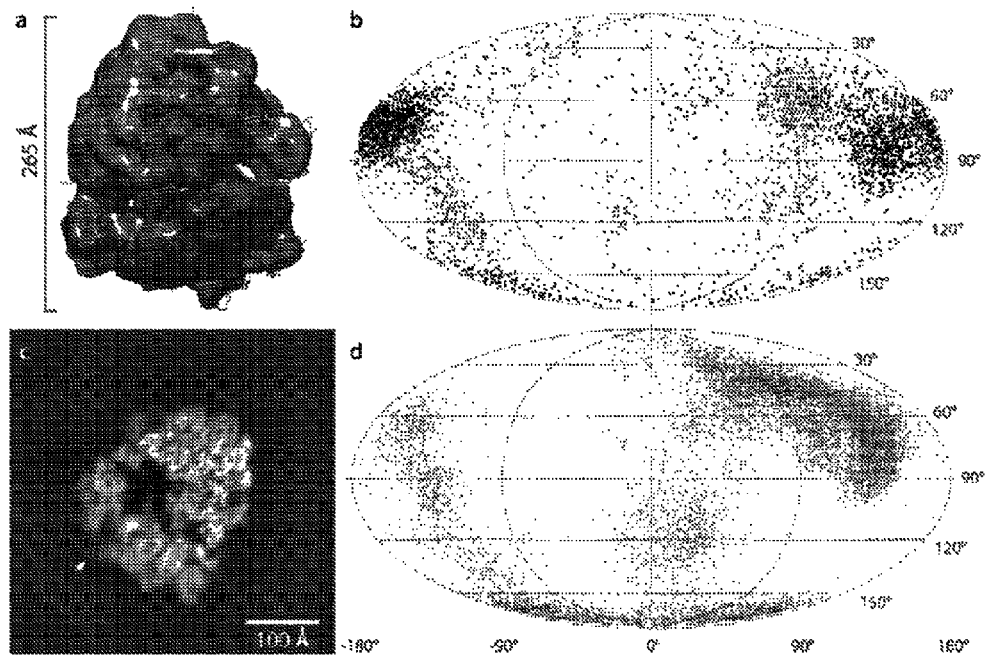

FIG. 4 shows analysis of ribosome structural data on plasma treated graphene. Panel a shows a 3D rendering of the electron density map of the *T. thermophilus* 70S ribosome, reconstructed to 19 Å from three micrographs of particles on graphene. The overlaid ribbon diagram is the rigid-body fit of the crystal structure to the map. Panel b is an equal area projection map of the orientation angles of the 2061 ribosomes relative to a graphene substrate (red dots) and an amorphous carbon substrate (black dots). Image c is a 1.3 Å slice through the unsharpened electron density map of the *S. cerevisiae* 80S ribosome reconstructed to 5.0 Å on graphene. Blurring of the 40S subunit (arrow) is due to conformational heterogeneity of the sample; this and non-optimal coverage of orientations in Fourier space limit the resolution of the map. Panel d is the projection map of the orientations of 20050 80S ribosomes on graphene (red dots) and on amorphous carbon (black dots).

Figure 5:
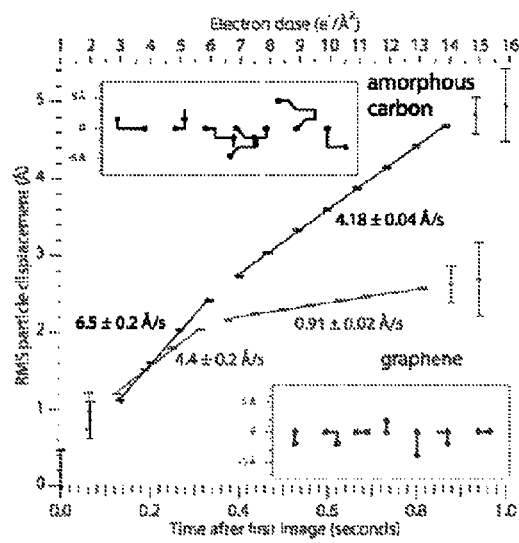

FIG. 5 shows reduced motion of proteins on graphene substrates. Protein particles in ice on graphene irradiated with high energy electrons exhibit two distinct phases of motion. The average 80S ribosome displacement from its initial position is plotted vs. time (dose) for both amorphous carbon (black \) and graphene (red –) substrates. Each point represents the RMS displacement of 20050 particles whose positions were measured using a five-frame running average under constant electron beam irradiation (300 keV; 16 e-/Å$^2$/s). Error bars for the fitted points are the standard error of the mean, and the error bars for the two points adjacent to each end are calculated from the fit intercepts (see methods). The insets show individual trajectories for seven randomly selected particles where the dots indicate the initial and final position of the particle (horizontal and vertical scales are the same; each trajectory origin is offset horizontally by 5 Å).

FIG. 6 show azimuthal integral intensity plots from selected area diffractograms. Plots are azimuthally integrated diffractograms taken before and after 80 s hydrogen plasma treatment used to measure change in lattice constant vis a vis conversion to graphane. The difference in 0-110 peak position, shown with arrows, is $-1.7 \times 10^{-3}$ Å$^{-1}$ which corresponds to a shift of −0.4% in lattice constant. This is less than the precision of the measurement from sample to sample, which is limited by the variation in lattice constant (std. dev.=0.9%) due to stretching of the graphene membrane on the grid.

Figure 7:
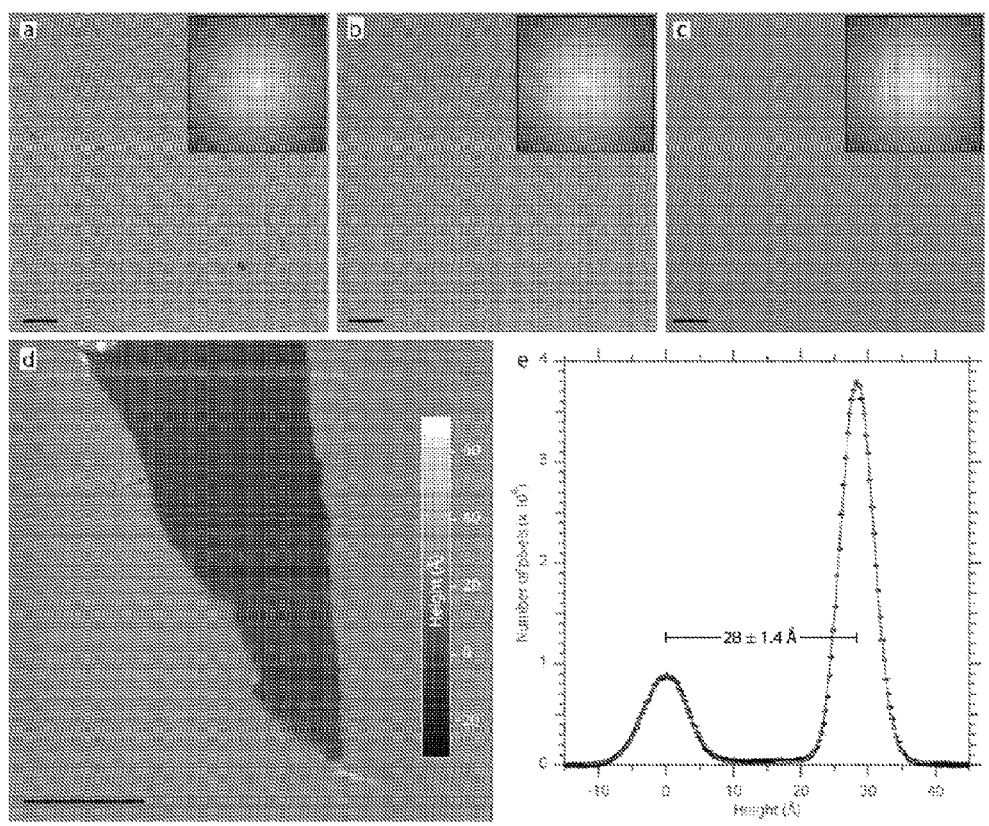

FIG. 7 shows low-dose images of carbon substrates. Panel a shows untreated graphene, panel b is the same sample as a after 30 second hydrogen plasma treatment. Panel c shows 28 Å thick amorphous carbon for comparison. Insets are the power spectra (FFTs) of each image, reduced to (1024 px)$^2$, and scale bars are all 2000 Å. Panel d is a contact mode AFM topography image of the edge of the carbon layer from c on a mica substrate, which was used to measure the thickness of the carbon layer accurately (scale bar is 5000 Å). Arrow (a) points to the edge of the cleaved carbon layer on the mica substrate. Panel e contains a histogram of the height values from d, with Gaussian fits to determine the thickness. The smaller red peak is the height of the mica substrate and the larger blue peak is the height on the amorphous carbon layer, and the difference is 28±1.4 Å.

Figure 8:
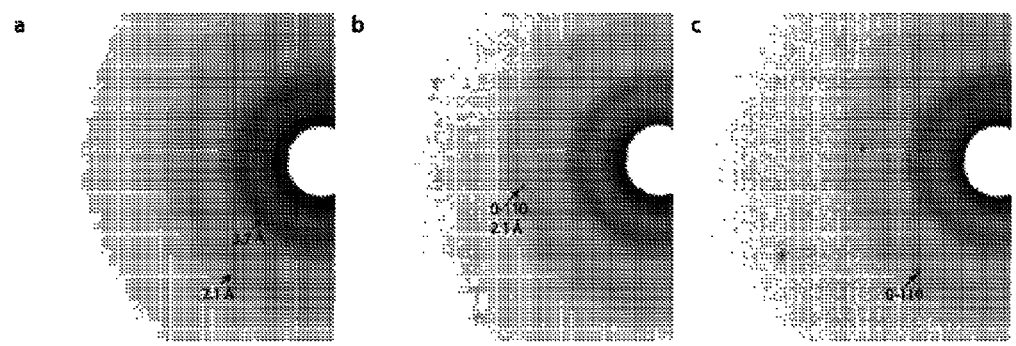

FIG. 8 shows electron diffractograms of ribosomes in ice. Panel a shows the selected area diffraction pattern from the suspended ice in FIG. 3a, where the first two diffuse Debye-Scherrer rings for amorphous ice at 3.70 Å and 2.14 Å are indicated with arrows[5]. The white disk at the center is the shadow of the primary beam stop, a homemade platinum ball on a wire. Panel b shows the diffraction pattern for the ribosomes in ice on suspended graphene in FIG. 3c, where the 0-110 reflection at 2.14 Å of the monolayer graphene is indicated, and sets the magnification scale for all three diffractograms. Similarly, panel c shows the diffractogram for the ribosomes in ice on suspended graphene for FIG. 3d, with the 0-110 peak indicated. Additional diffraction peaks are from small contaminant ice crystals on the surface of the thin film, which are visible in the micrographs. The camera length for each diffractogram is the same, nominally 47 cm.

Figure 9:
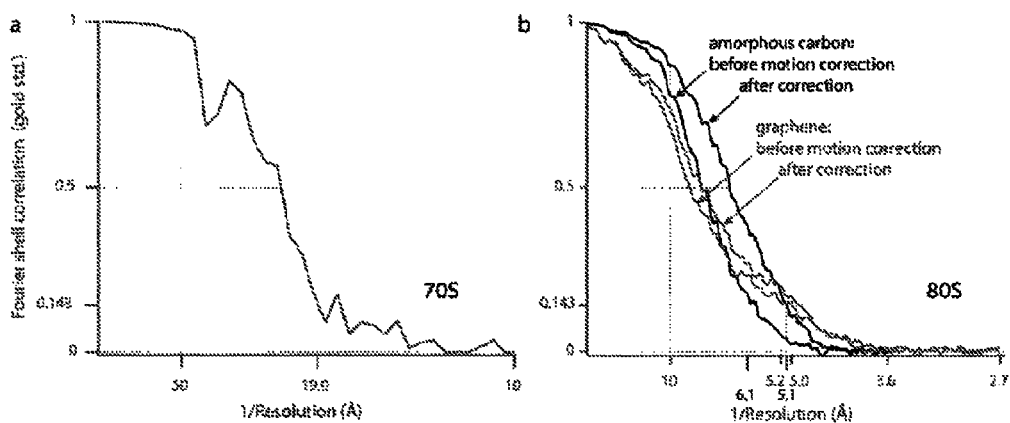

FIG. 9 shows Fourier shell correlation coefficients. Calculated for the 70S (a) and 80S (b) ribosomes using the reconstructed electron density map refined from two random halves of the dataset, keeping each separate through the reconstruction process ("gold standard")[41]. Using the 0.143 criterion[47], the resolution for the 70S map from 2061 particles on graphene using 3 micrographs was 19.0 Å. The resolution of the 80S map from 20,050 particles on graphene was 5.2 Å, and showed little improvement to 5.0 Å, with motion correction (b, red curves). We compare this to a reconstruction using the same number of particles chosen at random from a previously published dataset on the same ribosome sample where the resolution is 6.1 Å before motion correction and 5.1 Å after motion correction (black curves)[3].

Figure 10:
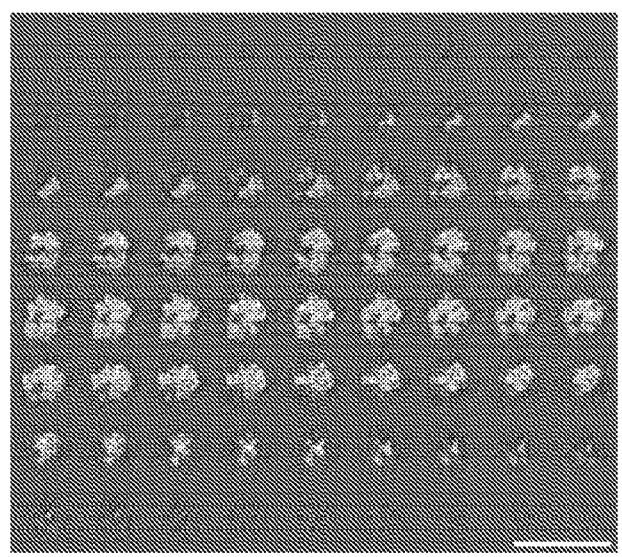

FIG. 10 shows a montage of 76 slices through the 70S ribosome electron density map. each slice is 4.58 Å thick and the scale bar is 500 Å.

EXAMPLES

Examples of embodiments of the invention are disclosed in detail herein, with reference to the accompanying drawings. It will be understood that the invention is not limited to the precise examples disclosed and that various changes and modifications can be effected therein by one skilled in the art without departing from the scope of the invention as defined by the appended claims and their equivalents.

Methods

Graphene Growth

Graphene was grown by chemical vapor deposition (CVD) on copper foil substrates[36,37]. Briefly, an ~18 cm$^2$ section of 25 μm copper foil (Alfa Aesar#13382) was placed in the 25 mm diameter quartz tube of a dry-pumped CVD furnace, evacuated to <20 mTorr, and then exposed to a continuous flow of Hydrogen (99.999%) gas at a flow of 20 sccm bringing the pressure in the reaction tube to 500 mTorr. The temperature of the oven was elevated under thermocouple control to 1000° C. over the course of ~15 minutes. Once the temperature was reached, an additional 20 sccm of methane (99.999%) was added to the reaction chamber for a duration of 15 minutes, bringing the total pressure to 700 mTorr. After methane addition was over, the heating was turned off and the reaction tube was slowly cooled to ambient temperature under continuing hydrogen flow over a period of 2 hours. Once cool, the hydrogen flow was stopped, the chamber vented with dry nitrogen and the graphene on copper foil was removed from the growth tube and stored in a critically-cleaned Fluorware wafer container inside a clean, low-humidity storage box until use.

Contact Angle Measurement

To measure the graphene water contact angle, individual 3.2 mm diameter disks were punched from the graphene on copper foils using a custom-made disk punch. Disks were initially cleaned by submersing them for 10 seconds in CMOS grade isopropyl alcohol (Sigma) and then after the residual solvent evaporated, were placed on a nitric acid cleaned glass slide inside a commercial plasma reaction chamber (Fischione Model 1070) where the grids were located 15±1 cm from the edge of the RF coils. The source of hydrogen was a high-purity electrolysis hydrogen generator (Dominik Hunter model 20HMD). Controls for the zero time exposure dose included those with and without various solvent cleaning treatments; we found the contact angle was the same for both to within experimental error. Each disk was mounted in the optical microscope (Zeiss Axiophot), a 1 μL droplet of 18 MOhm deionized water was applied and immediately (within 5 seconds) imaged upon withdrawal of the pipette tip using a calibrated digital camera attached to the microscope (Zeiss ERc5s). We measured the droplet evaporation rate (1.4 nL/sec) and found it contributed a negligible change in angle (<0.5°) during the delay between water application and image acquisition. Each image was subsequently analyzed to obtain the contact angle by graphically measuring the angle between the substrate plane and the tangent to the droplet at the point it met the surface. This measurement was performed 3-6 times for each of the plasma doses; the values were then normalized by dividing by the ratio of the droplet volume measured in the image to the value for the zero plasma dose. We found this normalization was required to correct for the error in pipetting this small of a volume. The multiple measurements were then averaged, and the standard deviation taken as the error in angle at each dose. Finally, we confirmed the presence of graphene covering the punched disks by subsequently transferring the graphene to EM grids as described below, and then imaging them with an electron microscope.

Graphene Grid Preparation

To create suspended monolayer graphene EM grids, we use a method based on one first described by Regan et al.[38]

and further developed in reference 30. We started by cleaning commercial holey carbon on 300 mesh gold grids (Quantifoil Au 300 1.2/1.3) by using anti-capillary tweezers to immerse them individually in chloroform, acetone and isopropyl alcohol for ~15 seconds each (Sigma-Aldrich, ultra-high purity semiconductor grade solvents). We found this helped to remove any residual photoresist and large surface contaminants remaining on the Quantifoil films after manufacture. After blotting dry in air, we then mounted the grids in a custom-made stainless steel suspension holder inside the plasma reactor mentioned above. The chamber was evacuated to <$10^{-5}$ Torr and then ultra high purity argon and oxygen (BOC 99.9999%) were admitted in a mass ratio of 9:1 to a steady state pressure of 21 mTorr. The auto-tuned RF plasma was sparked at 40 Watts (<3 W reverse power) and applied for the specified time. Quantifoil grids were then used immediately for graphene transfer. To cover the Quantifoil grid with a graphene monolayer, a 3.2 mm disk of graphene on copper was cut from a larger foil using a custom made mechanical punch. The disk was immersed in acetone, and isopropanol (Sigma, CMOS grade) for 10-15 seconds each and blotted dry prior to use. The plasma cleaned Quantifoil grid was then applied, carbon side down, to the disk. An optical microscope (Zeiss Axiophot) was used to inspect the grid "sandwich" making sure that both the grid and the disk were flat, free of particulate contaminants and in good contact with each other before the next step. Then 7 uL of CMOS grade isopropyl alcohol was added to the top of the grid, and the droplet was allowed to dry in air. The receding meniscus of the alcohol pulled the carbon film of the Quantifoil in contact with the graphene surface, which was verified by the change in the color of the reflected light from the surface. Next the grid-disk sandwich was floated in ~50 mL of buffered $FeCl_3$ (Sigma) in a crystallization dish for 20 min. The grid was then transferred with a flamed Pt loop to 32% HCl (Sigma CMOS grade) for 5 min, then 10% HCl for 5 min followed by 3 rinses in 18 MOhm deionized water. After the final water step, the grid was transferred using the loop to a piece of filter paper (Whatmann #1) in an acid washed, glass petri dish and stored in a low-humidity box until use.

Diffraction Studies of Hydrogen Treated Suspended Graphene

Selected area diffraction studies of suspended graphene were performed before and after hydrogen plasma exposure in the following way: First, CVD-grown graphene was transferred to a pre-cleaned Quantifoil grid as described above. The grid was mounted in a single-tilt holder (FEI) that had been cleaned with a 75%/25% Ar/O2 plasma at 50 W for 5 min. The grid was imaged with 300 keV electrons in a FEI Tecnai F30 microscope whose residual column pressure was nominally 88 nTorr (measured at the closest ion pump) and with an anti-contamination shield surrounding the sample cooled by liquid nitrogen. Selected area diffractograms were collected on a liquid cooled 2K×2K CCD camera (Tietz F224HD) using a fluence of ~30 e/Å$^2$/s, a nominal camera length of 690 mm, exposure time of 1 second, and a 10 µm diameter selected area aperture which corresponded to an interrogated area of 0.30 µm$^2$ at the sample. The actual camera length was calibrated using the 111 to 311 lattice reflections of a thin film of polycrystalline aluminum. After the first diffractogram was collected, the sample was removed from the column and immediately transported in a sealed, carefully cleaned container while still mounted in the holder to the plasma chamber, exposed to hydrogen plasma while mounted in the holder, and then immediately returned to the electron microscope for collection of the second data set. During repeated experiments using this transfer process we saw no evidence of contamination of the graphene sample. Final diffractograms were inverted to black on white to improve contrast when printed.

Vitrification and Cryo-Electron Microscopy Using Hydrogen Plasma Treated Graphene Grids Frozen stocks of *Thermus thermophilus* 70S ribosomes provided by the V. Ramakrishnan lab[33] were thawed and diluted to a concentration of 70 nM, in 5 mM HEPES pH 7.5, 50 mM KCl, 10 mM NH4Cl, 10 mM MgOAc, 6 mM BME, all the while being kept on ice. Graphene grids were treated with a pure hydrogen plasma as described above, for the indicated times just prior to use. Grids were placed in a cryoplunger (FEI Vitrobot IV) equilibrated to 4° C. and 100% relative humidity; 3 µL of sample was applied, allowed to incubate for 60 seconds, blotted with force −20 for 2 seconds and then plunged into liquid ethane at just above its melting point. Grids were then stored in liquid nitrogen until they were transferred to an FEI Polara electron microscope for imaging. Vitrified ribosomes were imaged with 300 keV electrons under very low-dose conditions (2.5 e−/Å$^2$/s; <0.2 e/Å$^2$ preexposure in low-mag mode) at a nominal magnification of 23 kX at a temperature of ~80-90K. Exposures were 1 second on a CMOS direct-electron detector (FEI back-thinned Falcon II) where the calibrated pixels corresponded to (4.58 Å)$^2$ at the sample.

Single Particle Data Analysis and Model Fits 2282 particles were picked from three micrographs using EMAN2's boxer program with the semiautomated swarm method[39]. Next, the particles were preprocessed and extracted in 76×76 pixel boxes (scale is 4.58 Å/px) in Relion[40], which included CTF fitting using CTFFIND3[41]. After one round of 2D classification with 18 classes, 221 particles were discarded and the remaining 2061 were used for 3D refinement. The 3D refinement was carried out in Relion using an initial model generated from the crystal structure from reference 33, low-pass filtered to 50 Å. The 3D refinement converged at an estimated angular accuracy of 3.6° and a resolution of 19.3 Å. The final map was low pass filtered to 19.3 Å. The angles assigned to each particle imaged in the final refinement iteration (rotation and tilt in Relion) were used to generate the plot of orientations. A combined PDB from 2WDK and 2WDL was fit to the map using UCSF Chimera's rigid body fitting algorithm[43]. The 3D renderings of the maps and models were created in Chimera.

Example 1

Hydrogenation of Graphene

In this example we demonstrate a method for making a partially hydrogenated graphene.

We apply a hydrogen ion or hydrogen atom to the surface of the graphene (in this example by a hydrogen plasma).

The hydrogen plasma is applied at an energy in the range 1 to 21 eV.

Figure 1:
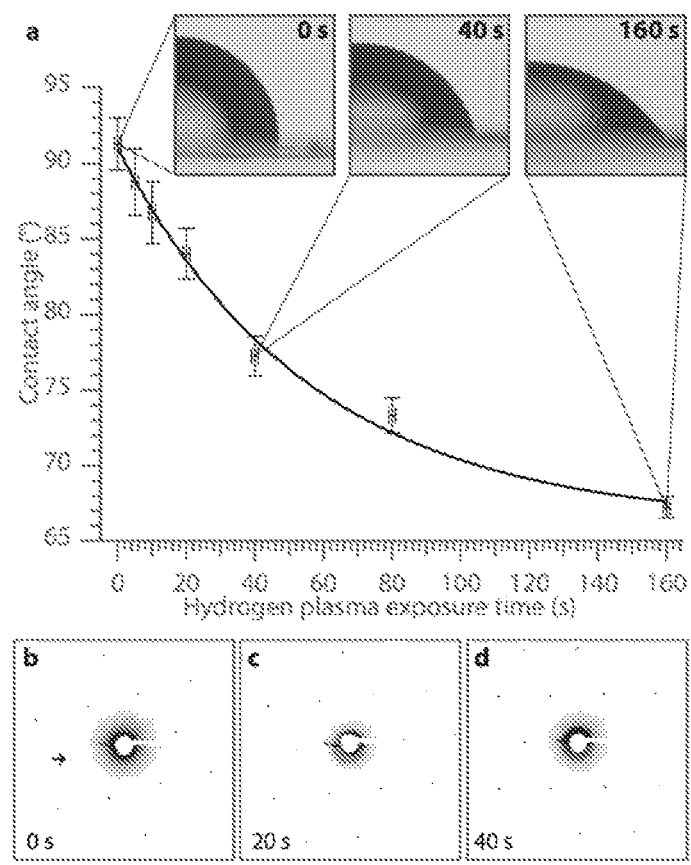
FIG. 1 shows characterization of graphene after low-energy hydrogen plasma treatment.

To measure the change in hydrophobicity of a graphene surface in response to hydrogenation (in this example by a hydrogen plasma), we measured the static contact angle between water, air and graphene as grown by CVD on a copper substrate. A 1 µl water droplet was applied to graphene on copper and imaged using a calibrated optical microscope attached to a digital camera (FIG. 1a insets). Each measurement was repeated for sequentially increasing doses of exposure to a pure hydrogen plasma at 50 mTorr and with energy (electron temperature) estimated to be approx. 10-15 eV, as detailed in the methods. The results of these measurements are shown in FIG. 1a. We found that the contact angle decreases exponentially from a value of 91±1.7° to a saturation value of 66±1.3° with a rate constant of 1/56 seconds. A contact angle of 91° for intrinsic graphene (FIG. 1a) is well within the wide range of reported values for graphene[27], and contact angles in the 60-80° range are comparable to those typically used for protein deposition on amorphous carbon substrates[4].

The primary species present in a low energy hydrogen plasma are H, H$^+$, H2$^+$ H3$^+$ and free electrons[28]. Based on this fact and the observation that extended hydrogen plasma treatments of graphene fully convert it to graphane[13], we expect the primary chemical reaction of graphene with the plasma to be the direct hydrogenation of the graphene lattice via the reaction

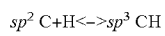

$$sp^2\ C+H<->sp^3\ CH$$

To monitor the conversion of the substrate lattice towards graphane, we measured the change in the lattice constant after plasma exposure using electron diffraction. The result is shown in FIG. 1b. After an 80 second dose of plasma treatment, the peak from 0-110 reflections of the graphene lattice broadens and shifts slightly towards lower frequencies (FIG. 6). The error in the measurement limits the precision to about 1%. Based on previous studies of graphane formation (where the lattice constant decreases by approx 5% upon full conversion to graphane[13]), this corresponds to an upper bound on the conversion of the carbon-carbon sp$^2$ bonds in the graphene to sp$^3$-H bonds of ~10% after an 80 second dose. Furthermore, the sharp peaks in the diffractograms after plasma treatment (FIG. 1c-d) demonstrate that the underlying graphene lattice is preserved. Interestingly, even a partial reduction of the graphene lattice to graphane induces a significant change in the hydrophobicity and saturates the reduction in contact angle. Using the Young-Dupré equation for the contact angle of a liquid droplet on a solid surface in a gas, we can use the contact angle measurements above to calculate the change in the water-graphene surface interfacial energy induced by the hydrogen plasma. The result is that a shift in contact angle from 91° for as-grown graphene on copper to a saturation value of 66° corresponds to a reduction in the graphene-water interfacial energy of 0.19±0.02 eV/nm$^2$.

Example 2

Graphene Cleaning

In this example we demonstrate that small atom plasma treatment such as hydrogen plasma treatment removes surface contaminants on graphene.

In particular we show a method for cleaning a graphene surface, comprising contacting said graphene surface with a hydrogen plasma. The time of contact is a time sufficient to remove surface impurities, as shown below.

We studied graphene's properties as a substrate for electron microscopy before and after plasma treatment, and compared it to amorphous carbon. Suspended graphene as transferred to a Quantifoil grid, when examined with electrons under conditions typical for imaging proteins (300 keV, 25 e-/Å$^2$, 39000× magnification), shows significant amounts of surface contamination (FIG. 2a and FIG. 7a). Exposing the graphene to 30 seconds of hydrogen plasma removes most of the surface contamination (FIG. 2b and FIG. 7b) but increases the background signal level in the image slightly due to the addition of hydrogen and perhaps some non-volatilized contaminant remnants (compare red and blue curves in FIG. 2c). Compared to a reasonably thin 28±1.4 Å layer of amorphous carbon (FIG. 2c and FIG. 7c-e), the background signal of the treated graphene lattice is significantly lower and featureless, with no Thon rings (FIG. 2c).

We note that hydrogen plasma removes or reduces surface contamination on graphene much faster than it modifies the graphene itself. This is because the hydrocarbon contaminants are easily broken down and volatilized by chemical reaction with the energetic plasma. Since the graphene sp$^2$ bond is highly resistant to chemical modification, it is only slowly reduced by atomic hydrogen in the plasma. Importantly, hydrogen species in the 10-15 eV range have insufficient energy to directly remove carbon atoms from their sp$^2$ bonds (approx. 21 eV) in the lattice[30-32], eliminating sputtering as a possible mechanism of damage to the bulk lattice.

Example 3

Tuning of Graphene Surface

In this example we show the control of the adsorption of proteins to graphene by partial hydrogenation of the graphene according to the present invention. Having shown that we can control the hydrophobicity of graphene, we then tested hydrogen plasma treated graphene as a substrate for cryo-EM using 70S ribosomes. We transferred monolayer graphene onto Quantifoil EM grids, subjected them to various doses of hydrogen plasma, and used them to prepare vitrified samples of 70S ribosomes. FIG. 3a shows that on grids without graphene, very few 70S particles are visible in the vitreous ice, as most are attracted to the surface of the Quantifoil carbon and the edges of the holes (note the ring of ribosomes at the edge of the hole). Using identical freezing and blotting conditions with graphene grids treated with 10 seconds of hydrogen plasma, only small patches of vitreous ice were visible (FIG. 3b). This is indicative of the incomplete wetting of the graphene surface and is consistent with the small change in contact angle at this dose (FIG. 1a). After 20 seconds of hydrogen plasma, graphene surfaces more uniformly wet and the ice quality is greatly improved, with approximately 600 ribosome particles per micrograph (1.2 μm diameter holes, FIG. 3c). This particle density (607 picked particles/μm$^2$) is far greater than on grids without graphene (57 picked particles/μm$^2$, compare FIGS. 3a and 3c) indicating that the 70S ribosomes adsorb to the graphene surface. The ring of particles around the edge of the hole is no longer present, indicating that the ribosomes uniformly adsorb to the hydrogen-treated graphene surface. A further increase of the plasma dose to 40 seconds leads to very densely packed ribosomes (approx. 1900 particles/μm$^2$, FIG. 3d). For the suspended ice in FIGS. 3a, c and d, selected area diffractograms were acquired after the first low dose image to demonstrate the vitreous nature of the ice and to verify the presence of the graphene layer (FIG. 8). Overall, these results show that there is a monotonic relationship between hydrogen plasma dose and surface particle density, when keeping other conditions uniform (blot time, humidity, etc.) thereby allowing the experimenter to use a graphene surface to tune particle distribution in the ice.

Example 4

Electron Microscopy Support Comprising Partially Hydrogenated Graphene

An electron microscopy support for receiving a biological sample is produced as described above. The support comprises support bars, and comprises graphene attached to said support bars, characterised in that said graphene is partially hydrogenated graphene, as described in the methods section above. Here we demonstrate use of this partially hydrogenated graphene as a substrate for cryo-EM. To verify the structural integrity of biological molecules adsorbed on the graphene surface, we determined the three dimensional structure of the 70S ribosome from three micrographs where the presence of the graphene support layer was verified by subsequent electron diffraction, including the one shown in FIG. 3c. Using 2061 particles picked from the three micrographs, we obtained a reconstructed electron density map at 19 Å resolution (FIG. 9a), which is depicted in FIG. 4a-c and FIG. 10. We fit the crystal structure of the 70S ribosome from Ref. 33 using rigid body fitting and found it matched the model well with no significant distortions in the molecule (FIG. 4d). Finally, we assessed the orientational distribution of the ribosomes on the graphene substrate using the angles assigned to each particle during the reconstruction. The result is plotted using a Molleweide equal area projection in FIG. 4e. While the ribosome exhibits preferential orientations on graphene, the orientational distribution compares favorably to similar data obtained under optimal conditions on glow-discharged amorphous carbon (shown in black in the projection map of FIG. 4b)[3].

Example 5

Improvement of Image Quality

Imperfections in particle images are often characterized using an empirical model of short-range motion. The model uses a Gaussian function to characterize loss of high resolution information where the empirically determined fitting parameter (Debye-Waller thermal parameter or B-factor) provides a measure of the image quality[33]. A number of variables can contribute to the B-factor including beam-induced particle movement, specimen charging, radiation damage and sample heterogeneity. Although the complicated nature of image distortion and particle motion is not well modeled mathematically by a simple Gaussian function, a change in B-factor is useful to characterize the improvement of a given method. We observed an ~35% (82 Å$^2$) reduction in B-factor of 80S ribosomes on graphene compared to amorphous carbon. Thus, graphene can be expected to improve the information content of any particle image.

To investigate the origins of the improved image quality, we analyzed the high-speed frame capture data collected for each micrograph. Our 80S data were acquired using a direct electron detector with 1 e-/Å$^2$/frame for 16 frames. Using a five-frame running average, we tracked the motion of each ribosome during the exposure. We calculated the ensemble average for each frame for all 20 050 particles in each dataset, and plot the trajectory in FIG. 5. Beam-induced movement of 80S particles has two linear phases which we fit separately in the plot. The slope of the lines is the speed of the movement, and FIG. 5 may occasionally be referred to as a 'speed plot' for this reason. 16 images per second are captured. The graphene in this example is 20s hydrogen treated, and corresponds to material used in FIG. 3(c). The initial fast phase has a speed of 4.4±0.2 Å/s ($\chi^2$=0.0018) on graphene prepared according to the invention and 6.5±0.2 Å/s ($\chi^2$=0.0027) on amorphous carbon. The speed of the second phase is 0.91±0.02 Å/s ($\chi^2$=0.00051) on graphene prepared according to the invention and 4.18±0.04 Å/s ($\chi^2$=0.0014) on amorphous carbon (amorphous carbon is prior art material included for comparative information showing superior performance of the invention). We omit the first and last two points from the fits since they are from three- and four-frame averages and therefore have significantly more error as indicated. Further, the assignment of the point of zero displacement to the position of the particle calculated for the first frame is somewhat arbitrary. The true initial particle position could also be taken as the y-intercept from the fit to the first phase of motion and would lead to a lower estimate of total particle displacement.

We hypothesise that the first phase of beam-induced particle movement is due to the complicated initial buildup of charge and stress on the specimen, which may include the buildup of large electric fields across regions of the irradiated area and density changes within the ice due to radiolysis ("charge-up phase"). In contrast, the steady-state speed of the second phase is likely governed by the mechanical response of the substrate to the apparently constant force induced by the beam ("mechanical-response phase"). Particle speeds for both phases are smaller for graphene: an ~30% reduction during the initial charge up phase and a nearly five-fold reduction during the mechanical-response phase. This is remarkable and surprising and is better even than the inventors expected.

We also used newly developed motion correction algorithms[3] to correct for particle motion during 3D reconstruction. We found that this did not significantly improve the map for graphene data, whereas the same algorithms applied to the same sample on amorphous carbon did result in significant improvement of the reconstruction (FIG. 9b). This agrees with the fact that we have reduced the motion of the particles according to the invention, so motion correction is less effective.

Thus we show excellent performance according to the invention, and by direct comparison to the prior art. The invention provides more information in every image. The invention provides more resolution in every image. The invention provides more signal in every image. The invention permits particles to be aligned more easily. Thus numerous technical benefits are delivered according to the invention.

SUMMARY

In these examples, we have demonstrated that partial hydrogenation (such as using a low-energy hydrogen plasma) can nondestructively modify graphene hydrophobicity to allow the interaction of biological molecules. Even the addition of about one hydrogen atom for every 20 carbon atoms induces a significant change in the hydrophobicity and induces adsorption of proteins to the surface (e.g. 20 s dose, FIG. 3c). To understand the large change in interfacial energy and the saturation of the contact angle with only partial hydrogenation of the lattice, we propose the following model. The water-graphene interfacial energy is dominated by hydrophobic interactions between water and the non-polar graphene lattice. Adding hydrogens to the lattice disrupts the order of water molecules near the graphene surface. Each hydrogen addition reduces the interfacial energy until the separation between the hydrogens becomes comparable to the length scale of the coordination of water near the hydrophobic surface. If we take the average energy of a hydrogen bond in water[34] at 300K to be ≅0.21 eV, then the change in interfacial energy we measure represents the addition of about 0.90 hydrogen bonds worth of energy per nm$^2$ to the interface. This distance corresponds to the length scale of the hydrophobic interaction in water[35], which decays exponentially with a decay constant of 1.0±0.1 nm. This leads us to conclude that the hydrogen plasma treatment primarily makes the graphene lattice hydrophilic by adding hydrogens that disrupt the local ordering of water molecules in solution.

These same hydrogens also likely control the protein distribution on the graphene surface by providing sites for the hydrogen-bonding of the molecules to the surface. A major problem in cryo-EM is the precise control of the distribution of proteins within a thin layer of vitreous ice. During blotting and vitrification, proteins often segregate to the air/water interface or to carbon support membranes. We show that the partial hydrogenation of a graphene lattice can induce adsorption of proteins from an aqueous solution, enabling control of particle surface density independent of other variables in cryo-EM sample preparation (humidity, blot time, etc.). By tuning their adsorption to the graphene, we remove the problems associated with protein aggregation and denaturation at air/water interfaces. Graphene is effectively invisible at resolutions used in structural biology (>2.1 Å) and it eliminates the problems associated with amorphous carbon including irreproducibility, charging and increased background noise. Further, we show that a low-energy hydrogen plasma can selectively remove surface contaminants much faster than it can reduce the graphene lattice itself. Graphene, as treated with a low-energy hydrogen plasma, is a reproducible and tunable surface for the adsorption of proteins.

Another major problem in cryo-EM is degradation of image quality and this is improved in two ways using graphene substrates according to the invention. First, graphene is effectively invisible at resolutions used in structural biology (<1/2.1 Å) and when it is used instead of amorphous carbon, it reduces the background signal. Second, graphene reduces beam-induced particle movement and thus increases the high resolution structural information available in each image. Ribosomes imaged on graphene exhibit two phases of beam-induced motion, both of which are significantly reduced relative to typical amorphous carbon substrates. The ~30% reduction in the initial "charge-up phase" is likely due to the high conductivity of the graphene film reducing the initial buildup of charge in and on the ice. And the five-fold reduction in particle speed during the second "mechanical-response phase" can be explained by the increased mechanical strength of graphene (1 TPa)[19,20] compared to amorphous carbon (~50-200 MPa)[36] but also likely involves a reduction in the electrically induced stresses in the sample due to a reduction in charge buildup. Further work to elucidate the detailed dynamics and underlying mechanisms of these particle motions will be of great interest. Both these and other advantages flow from the key contribution made by the invention of rendering graphene suitable for use with biological samples via partial hydrogenation.

On this basis, the invention provides for the preparation of biological specimens for electron microscopy to be improved from a trial-and-error prior art strewn with problems and lacking realistic expectation of success, to a systematic process of tuning of surface conditions helping to preserve the structural integrity of the proteins and the quality of the images.

The work leading to this invention has received funding from the European Research Council Under the European Union's Seventh Framework Programme (FP7/2007-2013)/ERC Grant Agreement no 261151.

REFERENCES

1. Grigorieff, N. & Harrison, S. C. Near-atomic resolution reconstructions of icosahedral viruses from electron cryomicroscopy. *Curr. Opin. Struct. Biol.* 21, 265-273 (2011).
2. Campbell, M. G. et al. Movies of ice-embedded particles enhance resolution in electron cryomicroscopy. *Structure* 20, 1823-1828 (2012).
3. Bai, X.-C., Fernandez, I. S., McMullan, G. & Scheres, S. H. Ribosome structures to near-atomic resolution from thirty thousand cryo-EM particles. *eLife* 2, e00461 (2013).
4. Dubochet, J., Groom, M. & Mueller-Neuteboom, S. in *Advances in Optical and Electron Microscopy* (Barer, R. & Cosslett, V. E.) 8, 107-135 (Academic Press, 1982).
5. Dubochet, J. et al. Cryo-electron microscopy of vitrified specimens. *Q. Rev. Biophys.* 21, 129-228 (1988).
6. Adrian, M., Dubochet, J., Lepault, J. & McDowall, A. W. Cryo-electron microscopy of viruses. *Nature* 308, 32-36 (1984).
7. Henderson, R. & McMullan, G. Problems in obtaining perfect images by single-particle electron cryomicroscopy of biological structures in amorphous ice. *Microscopy* 62, 43-50 (2013).
8. Brilot, A. F. et al. Beam-induced motion of vitrified specimen on holey carbon film *Journal of Structural Biology* 177, 630-637 (2012).
9. Brink, J., Sherman, M. B., Berriman, J. & Chiu, W. Evaluation of charging on macromolecules in electron cryomicroscopy. *Ultramicroscopy* 72, 41-52 (1998).
10. Downing, K. H., McCartney, M. R. & Glaeser, R. M. Experimental characterization and mitigation of specimen charging on thin films with one conducting layer. *Microsc. Microanal.* 10, 783-789 (2004).
11. Taylor, K. A. & Glaeser, R. M. Retrospective on the early development of cryoelectron microscopy of macromolecules and a prospective on opportunities for the future. *Journal of Structural Biology* 163, 214-223 (2008).
12. Geim, A. K. Graphene: status and prospects. *Science* 324, 1530-1534 (2009).
13. Elias, D. C. et al. Control of graphene's properties by reversible hydrogenation: evidence for graphane. *Science* 323, 610-613 (2009).
14. Grassucci, R. A., Taylor, D. J. & Frank, J. Preparation of macromolecular complexes for cryoelectron microscopy. *Nat Protoc* 2, 3239-3246 (2007).
15. Frank, J. *Three-Dimensional Electron Microscopy of Macromolecular Assemblies: Visualization of Biological Molecules in Their Native State*. (Oxford University Press, USA, 2006).
16. Curtis, G. H. & Ferrier, R. P. The electric charging of electron-microscope specimens. *Brit. J. Appl. Phys.* 2, 1035-1040 (1969).
17. Robertson, J. Amorphous carbon. *Advances in Physics* 35, 317-374 (1986).
18. Miyazawa, A., Fujiyoshi, Y., Stowell, M. & Unwin, N. Nicotinic acetylcholine receptor at 4.6 A resolution: transverse tunnels in the channel wall. *J. Mol. Biol.* 288, 765-786 (1999).
19. Lee, C., Wei, X., Kysar, J. W. & Hone, J. Measurement of the elastic properties and intrinsic strength of monolayer graphene. *Science* 321, 385-388 (2008).
20. Suenaga, K. & Koshino, M. Atom-by-atom spectroscopy at graphene edge. *Nature* 468, 1088-1090 (2010).
21. Russo, C. J. A structural imaging study of single DNA molecules on carbon nanotubes. Thesis, Harvard University (2010).
22. Pantelic, R. S., Meyer, J. C., Kaiser, U., Baumeister, W. & Plitzko, J. M. Graphene oxide: A substrate for optimizing preparations of frozen-hydrated samples. *Journal of Structural Biology* 170, 152-156 (2010).

23. Pantelic, R. S. et al. Graphene: Substrate preparation and introduction. *Journal of Structural Biology* 174, 234-238 (2011).
24. Pantelic, R. S., Suk, J. W., Hao, Y., Ruoff, R. S. & Stahlberg, H. Oxidative Doping Renders Graphene Hydrophilic, Facilitating Its Use As a Support in Biological TEM. *Nano Lett.* 11, 4319-4323 (2011).
25. Gómez-Navarro, C. et al. Electronic transport properties of individual chemically reduced graphene oxide sheets. *Nano Lett.* 7, 3499-3503 (2007).
26. Burgess, J. S. et al. Tuning the electronic properties of graphene by hydrogenation in a plasma enhanced chemical vapor deposition reactor. *Carbon* 49, 4420-4426 (2011).
27. Taherian, F., Marcon, V., van der Vegt, N. F. A. & Leroy, F. What is the contact angle of water on graphene? *Langmuir* 29, 1457-1465 (2013).
28. Méndez, I., Gordillo-Vazquez, F. J., Herrero, V. J. & Tanarro, I. Atom and ion chemistry in low pressure hydrogen dc plasmas. *J Phys Chem A* 110, 6060-6066 (2006).
29. Reimer, L. & Kohl, H. *Transmission Electron Microscopy.* (Springer Verlag, 2008).
30. Russo, C. J. & Golovchenko, J. A. Atom-by-atom nucleation and growth of graphene nanopores. *Proc. Natl. Acad. Sci. U.S.A.* 109, 5953-5957 (2012).
31. Krasheninnikov, A. V. & Banhart, F. Engineering of nanostructured carbon materials with electron or ion beams. *Nat Mater* 6, 723-733 (2007).
32. Xie, L., Jiao, L. & Dai, H. Selective etching of graphene edges by hydrogen plasma. *J. Am. Chem. Soc.* 132, 14751-14753 (2010).
33. Voorhees, R. M., Weixlbaumer, A., Loakes, D., Kelley, A. C. & Ramakrishnan, V. Insights into substrate stabilization from snapshots of the peptidyl transferase center of the intact 70S ribosome. *Nat. Struct. Mol. Biol.* 16, 528-533 (2009).
34. Pauling, L. *General Chemistry.* (W.H. Freeman and Co., 1970).
35. Israelachvili, J. & Pashley, R. The hydrophobic interaction is long range, decaying exponentially with distance. *Nature* 300, 341-342 (1982).
36. Reina, A. et al. Large area, few-layer graphene films on arbitrary substrates by chemical vapor deposition. *Nano Lett.* 9, 30-35 (2009).
37. Li, X. et al. Large-Area Synthesis of High-Quality and Uniform Graphene Films on Copper Foils. *Science* 324, 1312-1314 (2009).
38. Regan, W. et al. A direct transfer of layer-area graphene. *Appl. Phys. Lett.* 96, 113102 (2010).
39. Tang, G. et al. EMAN2: an extensible image processing suite for electron microscopy. *Journal of Structural Biology* 157, 38-46 (2007).
40. Scheres, S. H. W. RELION: implementation of a Bayesian approach to cryo-EM structure determination. *Journal of Structural Biology* 180, 519-530 (2012).
41. Mindell, J. A. & Grigorieff, N. Accurate determination of local defocus and specimen tilt in electron microscopy. *Journal of Structural Biology* 142, 334-347 (2003).
42. Rosenthal, P. B. & Henderson, R. Optimal determination of particle orientation, absolute hand, and contrast loss in single-particle electron cryomicroscopy. *J. Mol. Biol.* 333, 721-745 (2003).
43. Pettersen, E. F. et al. UCSF Chimera—a visualization system for exploratory research and analysis. *J Comput Chem* 25, 1605-1612 (2004).
44. Israelachvili, J. N. *Intermolecular and Surface Forces.* (Academic Press, 2011).
45. Shih, C.-J. et al. Breakdown in the wetting transparency of graphene. *Phys. Rev. Lett.* 109, 176101 (2012).
46. Cui, Y. et al. Nanowire Nanosensors for Highly Sensitive and Selective Detection of Biological and Chemical Species. *Science* 293, 1289-1292 (2001).
47. Patolsky, F. et al. Electrical detection of single viruses. *P Natl Acad Sci USA* 101, 14017-14022 (2004).
48. Stern, E. et al. Label-free immunodetection with CMOS-compatible semiconducting nanowires. *Nature* 445, 519-522 (2007).
49. Choi, Y. et al. Single-Molecule Lysozyme Dynamics Monitored by an Electronic Circuit. *Science* 335, 319-324 (2012).
50. Schedin, F. et al. Detection of individual gas molecules adsorbed on graphene. *Nat Mater* 6, 652-655 (2007)
51. Ohno, Y., Maehashi, K., Yamashiro, Y. & Matsumoto, K. Electrolyte-Gated Graphene Field-Effect Transistors for Detecting pH and Protein Adsorption. *Nano Lett* 9, 3318-3322 (2009).
52. Zheng et al. Multiplexed electrical detection of cancer markers with nanowire sensor arrays. *Nat Biotech* 23, 1294-1301 (2005)

The invention claimed is:

1. A support for receiving a biological sample, the support comprising:
    at least one support member, and
    graphene attached to said at least one support member, wherein the graphene is partially hydrogenated graphene, wherein said graphene is 1% to 10% hydrogenated graphene.

2. The support according to claim 1, wherein said graphene is 3% to 10% hydrogenated graphene.

3. The support according to claim 1, wherein the at least one support member is attached to a support film, and the graphene is attached to said support film.

4. An electron microscopy support, comprising:
    the support according to claim 3, wherein said support film comprises carbon.

5. The support according to claim 1, wherein said partially hydrogenated graphene comprises at least a first area of graphene and at least one further area of graphene, wherein said first area is hydrogenated to a first hydrogenation value, and said at least one further area is hydrogenated to a different hydrogenation value.

6. The support according to claim 1, further comprising a biological molecule adsorbed to said partially hydrogenated graphene.

7. The support according to claim 1, wherein the partially hydrogenated graphene is formed as a surface configured to support a biological molecule for electron microscopy.

8. A method for making a partially hydrogenated graphene, wherein said graphene is 1% to 50% hydrogenated graphene, the method comprising:
    applying a hydrogen ion or hydrogen atom to the surface of graphene, wherein the hydrogen ion or hydrogen atom is applied at an energy in the range 1 to 21 eV, wherein said hydrogen ion or hydrogen atom is applied in the form of hydrogen plasma and said graphene is contacted with said hydrogen plasma for 10 to 40 seconds.

9. The method according to claim 8, wherein the energy is in the range 1 to 14 eV.

10. The method according to claim 8, wherein said graphene is contacted with said hydrogen plasma for 18 to 22 seconds.

11. The method according to claim 8, wherein said graphene is graphene mounted on an electron microscopy support.

12. Partially hydrogenated graphene obtained by the method according to claim 8.

13. A sensor, comprising:
a surface capable of adsorbing a biological molecule thereto, wherein said surface includes partially hydrogenated graphene, wherein said graphene is 1% to 10% hydrogenated graphene.

14. The sensor according to claim 13, wherein said graphene is 3% to 10% hydrogenated graphene.

15. The support according to claim 1, which is an electron microscopy (EM) support.

16. A sensor, comprising:
the support according to claim 1.

17. A method for cleaning a graphene surface, comprising:
contacting said graphene surface post-synthesis with a hydrogen plasma or a helium plasma or a neon plasma for a time sufficient to remove surface impurities.

18. The method according to claim 17, wherein said plasma is at an energy in the range 1 to 14 eV.

19. The method according to claim 17, wherein said plasma is an inert plasma.

20. The method according to claim 19, wherein said plasma is neon plasma.

21. The method according to claim 19, wherein said plasma is helium plasma.

22. The method according to claim 17, wherein said graphene surface is contacted with said plasma for 1 to 30 seconds.

23. The method according to claim 22, wherein said graphene surface is contacted with said plasma for 1 to 10 seconds.

24. The method according to claim 17, wherein said graphene is partially hydrogenated graphene.

25. Cleaned graphene obtained by the method according to claim 17.

26. The method according to claim 17, further including use of a hydrogen plasma at an energy in the range 1 to 14 eV for preparation of graphene for use in electron microscopy.

27. The method according to claim 26, wherein the graphene is prepared by partial hydrogenation.

28. A method of imaging a biological sample, the method comprising:
configuring said biological sample on the support according to claim 1;
arranging said support in an electron beam of an electron microscope; and
collecting image data.

29. An imaging apparatus operable to provide an electron microscopy image of a biological sample, said apparatus comprising:
the support according to claim 1 configured to mount a biological sample;
an electron microscope generating an electron beam arranged to be incident on said support; and
a collection device operable to collect image data.

30. The support according to claim 2, wherein said graphene is 5% hydrogenated graphene.

31. The sensor according to claim 14, wherein said graphene is 5% hydrogenated graphene.

32. The support according to claim 1, wherein the graphene is suspended graphene attached to the at least one support member.

33. The support accordingly to claim 1, wherein the support constitutes a transmission electron microscopy support.

34. The support accordingly to claim 33, wherein the graphene is one atom thick.

* * * * *